United States Patent
Mou et al.

(10) Patent No.: US 11,772,030 B2
(45) Date of Patent: *Oct. 3, 2023

(54) MINIATURE GAS DETECTION AND PURIFICATION DEVICE

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW); Chun-Yi Kuo, Hsinchu (TW); Yang Ku, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 187 days.

This patent is subject to a terminal disclaimer.

(21) Appl. No.: 17/171,110

(22) Filed: Feb. 9, 2021

(65) Prior Publication Data
US 2021/0245087 A1  Aug. 12, 2021

(30) Foreign Application Priority Data

Feb. 11, 2020 (TW) .................... 109104279

(51) Int. Cl.
*B01D 46/44* (2006.01)
*B01D 46/46* (2006.01)
(Continued)

(52) U.S. Cl.
CPC .............. *B01D 46/442* (2013.01); *A61L 9/00* (2013.01); *B01D 46/0028* (2013.01);
(Continued)

(58) Field of Classification Search
CPC ................ B60H 3/0078; B60H 3/0658; B60H 2003/0675; B60H 2203/0691;
(Continued)

(56) References Cited

U.S. PATENT DOCUMENTS

| 2011/0086118 | A1* | 4/2011 | Kim ...................... B01D 53/34 424/769 |
| 2015/0290572 | A1* | 10/2015 | Stoner, Jr. .......... B01D 46/4254 55/504 |
| 2017/0275472 | A1* | 9/2017 | Yeung ................. A01N 65/22 |

FOREIGN PATENT DOCUMENTS

| CN | 107894042 A | * | 4/2018 | ............. F24F 13/28 |
| CN | 139395477 A | | 3/2019 | |

(Continued)

OTHER PUBLICATIONS

CN209809754U_ENG (Espacenet machine translation of Mo) (Year: 2019).*

(Continued)

*Primary Examiner* — Gabriel E Gitman
(74) *Attorney, Agent, or Firm* — Birch, Stewart, Kolasch & Birch LLP

(57) ABSTRACT

A miniature gas detection and purification device is disclosed for a user to carry with himself, and includes a main body, a purification module, a gas guider and a gas detection module. The gas detection module detects gas of surrounding environment to obtain a gas detection datum, and controls the gas guider to be operated according to the gas detection datum, so that gas is inhaled into the main body and flows through the purification module for filtration and purification, and the gas purified is finally guided to a region close to the user.

22 Claims, 29 Drawing Sheets

(51) Int. Cl.
| | |
|---|---|
| *G01N 15/06* | (2006.01) |
| *B01D 46/00* | (2022.01) |
| *B03C 3/017* | (2006.01) |
| *B01D 53/04* | (2006.01) |
| *A61L 9/00* | (2006.01) |
| *G01N 15/02* | (2006.01) |
| *F24F 110/00* | (2018.01) |
| *F24F 8/80* | (2021.01) |

(52) U.S. Cl.
CPC ..... *B01D 46/0032* (2013.01); *B01D 46/0036* (2013.01); *B01D 46/0041* (2013.01); *B01D 46/46* (2013.01); *B01D 53/04* (2013.01); *B03C 3/017* (2013.01); *G01N 15/0211* (2013.01); *G01N 15/06* (2013.01); *A61L 2209/131* (2013.01); *A61L 2209/14* (2013.01); *B01D 2253/102* (2013.01); *B01D 2257/91* (2013.01); *B01D 2259/4541* (2013.01); *B01D 2279/40* (2013.01); *B01D 2279/65* (2013.01); *F24F 8/80* (2021.01); *F24F 2110/00* (2018.01); *G01N 2015/0693* (2013.01)

(58) Field of Classification Search
CPC . B60H 3/0608; A61L 9/00; A61L 8/16; A61L 2209/131; A61L 2209/111; A61L 9/205; A61L 2209/14; B03C 3/17; B03C 3/32; G01N 15/0211; G01N 15/06; G01N 15/0205; G01N 2015/0693; B01D 39/04; B01D 39/2055; B01D 46/0028; B01D 46/0032; B01D 46/0036; B01D 46/0041; B01D 46/0049; B01D 46/42; B01D 46/46; B01D 53/04; B01D 53/30; B01D 53/323; B01D 53/0407; B01D 2239/0442; B01D 2239/0478; B01D 2259/818; B01D 2259/4541; B01D 2257/708; B01D 2257/502; B01D 2257/504; B01D 2257/90; B01D 2257/91; B01D 2255/802; B01D 2253/102; B01D 2279/40; B01D 2279/65; F24F 8/10; F24F 8/80; F24F 2110/00; F24F 2110/64; F24F 2110/66
See application file for complete search history.

(56) References Cited

FOREIGN PATENT DOCUMENTS

| | | | |
|---|---|---|---|
| CN | 110501454 A | 11/2019 | |
| CN | 209809754 U * | 12/2019 | ............ B01D 46/00 |
| CN | 110732206 A | 1/2020 | |
| EP | 3473941 A1 * | 4/2019 | ............ A61L 9/205 |
| KR | 10-2016255 B1 | 8/2019 | |
| TW | M523072 U | 6/2016 | |
| TW | 567364 U * | 9/2018 | ............ G01N 21/17 |
| TW | 201920881 A | 6/2019 | |
| TW | I670045 B | 9/2019 | |
| WO | WO-2016004399 A1 * | 1/2016 | ......... B01D 46/0023 |
| WO | WO-2018100209 A2 * | 6/2018 | ............... G01N 1/22 |

OTHER PUBLICATIONS

TWM567364U_ENG (InnovationQ Plus machine translation of Mou) (Year: 2018).*
CN107894042A_ENG (Espacenet machine translation of Wang) (Year: 2018).*

* cited by examiner

MINIATURE GAS DETECTION AND PURIFICATION DEVICE

FIELD OF THE INVENTION

The present disclosure relates to a gas detection and purification device, and more particularly to a miniature gas detection and purification device for a user to carry with himself.

BACKGROUND OF THE INVENTION

Recently, people pay more and more attention to the quality of the air around their lives. For example, carbon monoxide, carbon dioxide, volatile organic compounds (VOC), PM2.5, nitric oxide, sulfur monoxide and even the suspended particles contained in the air that expose in the environment would affect the human health, and even harmful for the human life severely. Therefore, the quality of environmental air has attracted the attention of various countries. Currently, how to detect the air quality and avoid the harm accompany thereby is a problem that urgently needs to be solved.

In order to confirm the quality of the air, it is feasible to use a gas sensor to detect the air surrounding in the environment. If the detection information can be provided in real time to warn the people stay in the environment, it would be helpful for the people to prevent and/or evacuate from the hazard environment immediately and avoid from affecting the human health and the harm causing by the hazardous gas exposed in the environment. Therefore, it is a very good application to use a gas sensor to detect the air surrounding in the environment. The gas purification device is a solution for the air-pollution of modern people to prevent inhalation of the hazardous gas. Therefore, how to combine the gas purification device with a gas detection device so as to facilitate the user to carry with himself for detecting the air quality in real time, whenever and wherever, and provide the benefits of purifying the air in a region close to the user is a main developing subject in the present disclosure.

SUMMARY OF THE INVENTION

An object of the present disclosure is to provide a miniature gas detection and purification device for a user to carry with himself. The miniature gas detection and purification device includes a main body, a purification module, a gas guider and a gas detection module. The gas detection module detects gas in an environment surrounding the user to obtain a gas detection datum, for controlling the gas guider to perform the actuation operations. Thereby, the gas of environment surrounding the user is introduced into the main body and flows through the purification module for filtration and purification. Finally, the benefit of guiding the purified gas to a region close to the user is achieved.

In accordance with an aspect of the present disclosure, a gas detection and purification device including a main body, a purification module, a gas guider and a gas detection module is provided. The main body includes at least one inlet, at least one outlet, a detecting inlet, a detecting outlet and a gas-flow channel. The gas-flow channel is disposed between the at least one inlet and the at least one outlet. The purification module is disposed in the gas-flow channel of the main body. The gas guider is disposed in the gas-flow channel of the main body and located at a side of the purification module. Gas is inhaled through the at least one inlet, flows through the purification module for filtration and purification, and is discharged out through the at least one outlet. The gas detection module is disposed in the main body, spatially corresponding to the detecting inlet and the detecting outlet for detecting the gas to obtain a gas detection datum, and includes a gas detection main part, a processor, a communicator and a battery unit. The battery unit provides an operating power to the gas detection main part. The gas detection main part detects the gas introduced from the outside of the main body to obtain the gas detection datum, the processor receives the gas detection datum to calculate, process and control an enablement and disablement of the gas guider, and the communicator receives the gas detection datum from the processor. The processor controls operations of the gas guider in the enablement according to the gas detection datum detected by the gas detection module, so that the gas is inhaled through the detecting inlet and flows through the purification module for filtration and purification, and the gas purified is guided to a region close to the user.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
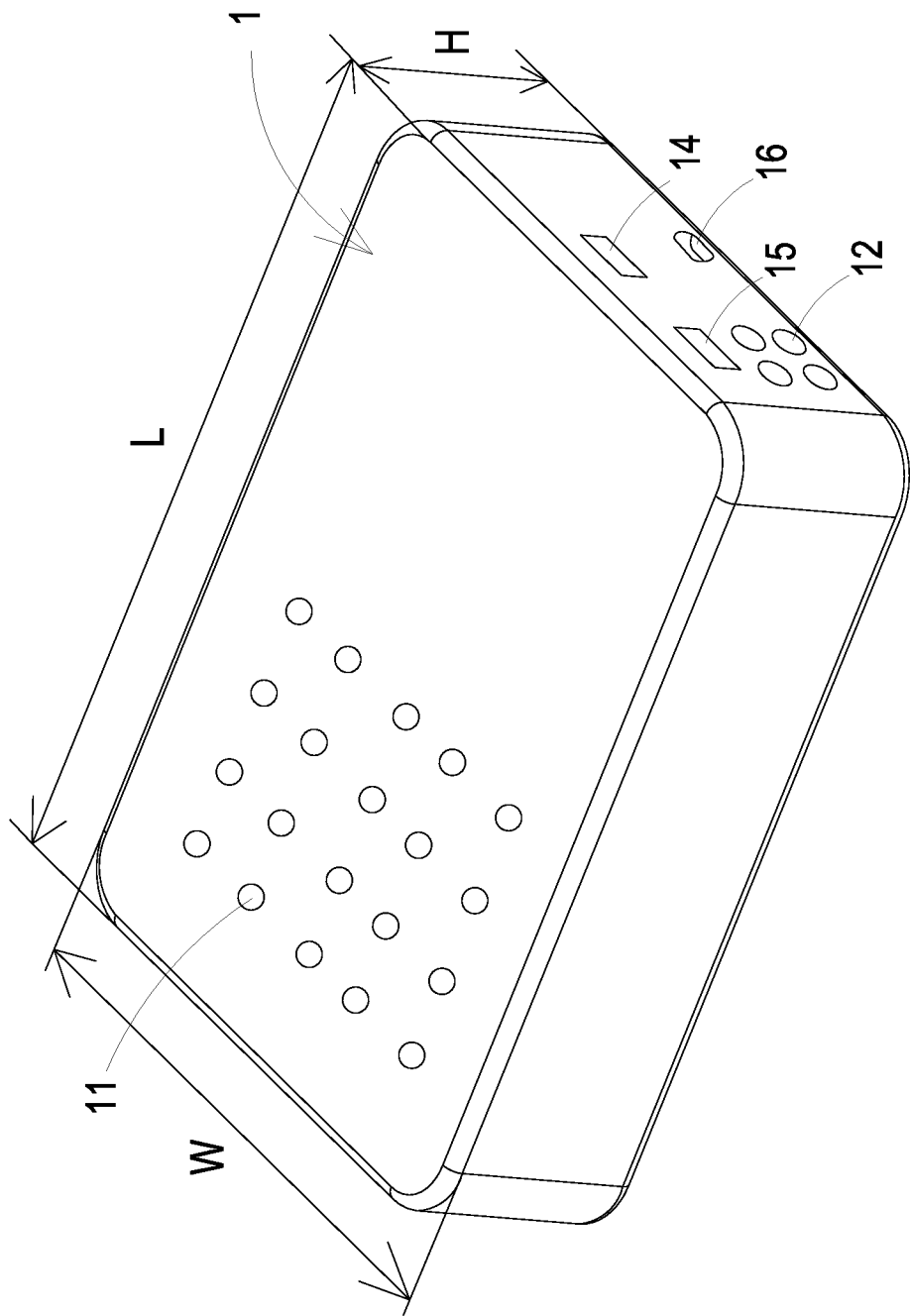
FIG. 1 is a schematic exterior view illustrating a miniature gas detection and purification device according to the embodiment of the present disclosure.
Figure 2A:
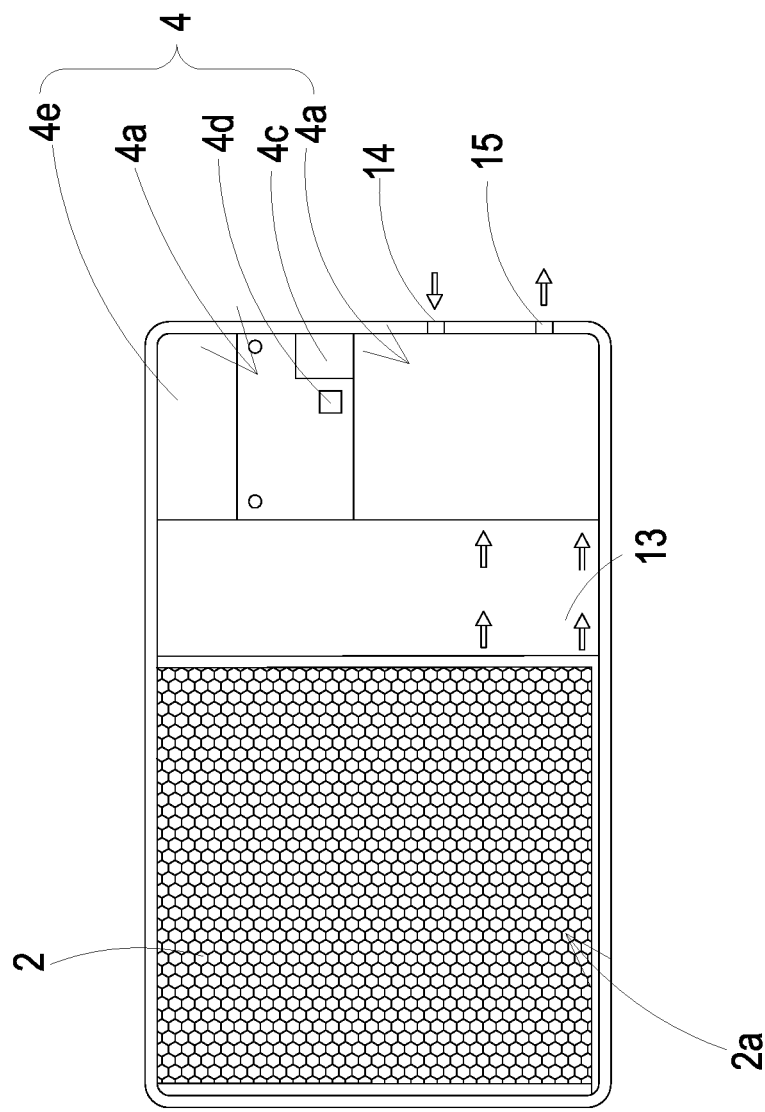
FIG. 2A is a schematic cross-sectional top view illustrating a purification module of the miniature gas detection and purification device according to the embodiment of the present disclosure.
Figure 2B:
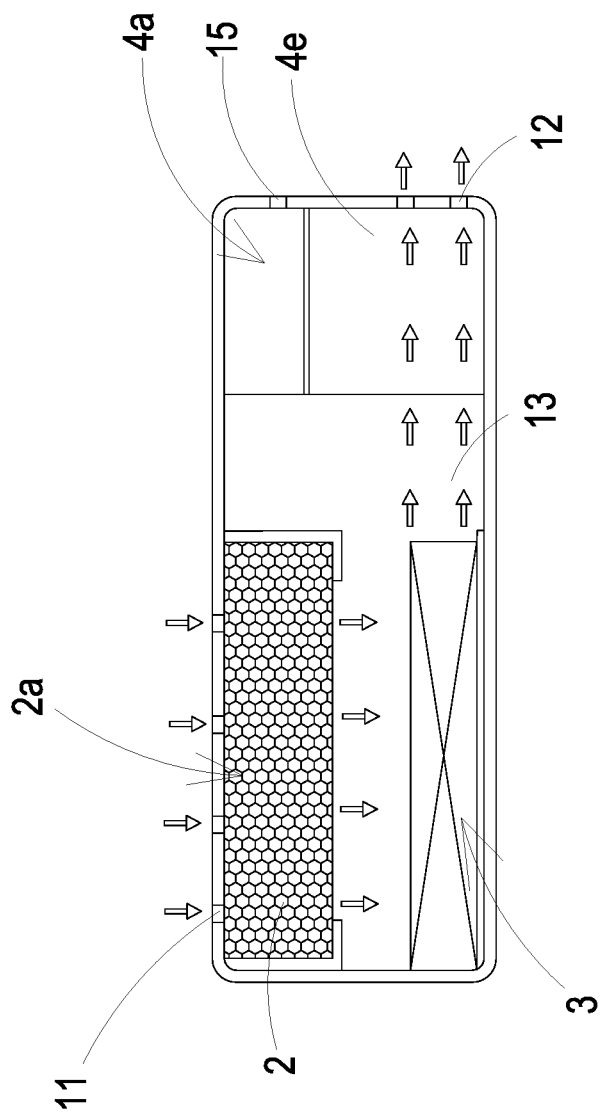
FIG. 2B is a schematic cross-sectional side view illustrating a purification module of the miniature gas detection and purification device according to the embodiment of the present disclosure.

Please refer to FIG. 1, FIG. 2A and FIG. 2B. The present disclosure provides a miniature gas detection and purification device including a main body 1, a purification module 2, a gas guider 3 and a gas detection module 4 for a user to carry with himself. Therefore, in the overall structure design, whether the volume is suitable for hand-holding or portability is considered. A length L, a width W, a height H and a weight of the main body 1 of the present disclosure are considered in the design thereof and according to the designing ability of arranging the purification module 2, the gas guider 3 and the gas detection module 4 into the main body 1. Preferably but not exclusively, in the embodiment, the main body 1 has the length L ranged from 75 mm to 110 mm, the width W ranged from 50 mm to 70 mm, and the height H ranged from 18 mm to 32 mm. Moreover, the main body 1 has the weight ranged from 150 g to 300 g. Preferably but not exclusively, in an embodiment, the main body 1 has the length L ranged from 85 mm to 95 mm, the width W ranged from 55 mm to 65 mm, and the height H ranged from 21 mm to 29 mm. Moreover, the main body 1 has the weight ranged from 100 g to 200 g. Preferably but not exclusive, in another embodiment, the main body 1 has the length L of 90 mm, the width W of 60 mm and the height H of 25 mm. Moreover, the main body 1 has the weight less than 300 g. The overall arrangement of the miniature gas detection and purification device is most suitable for the user to carry with himself.

Please refer to FIG. 1, FIG. 2A and FIG. 2B. In the embodiment, the main body 1 includes at least one inlet 11, at least one outlet 12 and a gas-flow channel 13. The gas-flow channel 13 is disposed between the at least one inlet 11 and the at least one outlet 12. In the embodiment, the main body 1 further includes a detecting inlet 14, a detecting outlet 15 and a buckle 16. The buckle 16 is buckled with a hanging belt (not shown) to be buckled and allows the main body 1 to be wore on the user to carry with himself.

Please refer to FIG. 2A and FIG. 2B. In the embodiment, the purification module 2 is disposed in the gas-flow channel 13 for filtering gas introduced through the gas-flow channel 13. The gas guider 3 is disposed in the gas-flow channel 13 and located at a side of the purification module 2. The gas is inhaled through the at least one inlet 11, flows through the purification module 2 for filtration and purification, and is discharged out through the at least one outlet 12.

Please refer to FIGS. 2A and 2B. The above-mentioned purification module 2 is disposed in the gas-flow channel 13. In the embodiment, the gas is introduced into the gas-flow channel 13 by the gas guider 3, and is filtered through the filter screen 2a to adsorb the chemical smoke, bacteria, dust particles and pollen contained in the gas, so as to achieve the effects of filtration and purification of air. Preferably but not exclusively, the filter screen 2a is one selected from the group consisting of an electrostatic filter screen, an activated carbon filter screen and a high efficiency particulate air (HEPA) filter screen. Furthermore, in an embodiment, the filter screen 2a is coated with a layer of a cleansing factor containing chlorine dioxide (e.g., AMS) to inhibit viruses and bacteria in the gas. Inhibition rates for Influenza A virus, Influenza B virus, Enterovirus and Norovirus are more than 99%, it is helpful for reducing cross-infection of viruses. In another embodiment, the filter screen 2a is coated with an herbal protective layer consisting of *Rhus chinensis* Mill extracts from Japan and *Ginkgo biloba* extracts to form an herbal protective anti-allergic filter. It can effectively resist allergies and destroy the surface protein of influenza virus (for example: H1N1 influenza virus) passing through the filter. In other embodiments, the filter screen 2a is coated with a silver ion to inhibit viruses and bacteria in the gas. In other embodiments, the filter screen 2a can consist of a high efficiency particulate air (HEPA) filter screen and an electrostatic filter screen, and is used to filter virus and bacteria in the air. In other embodiments, the filter screen 2a can be a module consisting of a high efficiency particulate air (HEPA) filter screen and one selected from the group consisting of a photo-catalyst, a voltage plasma, a negative ionizer and an ultraviolet (UV) lamp, and is used to filter or decompose virus and bacteria in the air. Consequently, the efficacy of purifying the gas is achieved.

In the embodiment, preferably but not exclusively, the gas guider 3 is a fan, such as a vortex fan or a centrifugal fan. Alternatively, the gas guider 3 is an actuating pump 30, as shown in FIGS. 3A, 3B, 4A and 4B. In the embodiment, the actuating pump 30 includes a gas inlet plate 301, a resonance plate 302, a piezoelectric actuator 303, a first insulation plate 304, a conducting plate 305 and a second insulation plate 306, which are stacked on each other sequentially. In the embodiment, the gas inlet plate 301 includes at least one inlet aperture 301a, at least one convergence channel 301b and a convergence chamber 301c. The at least one gas inlet aperture 301a is disposed to inhale the gas. The at least one gas inlet aperture 301a correspondingly penetrates through the gas inlet plate 301 into the at least one convergence channel 301b, and the at least one convergence channel 301b is converged into the convergence chamber 301c. Therefore, the gas inhaled through the at least one gas inlet aperture 301a is converged into the convergence chamber 301c. The number of the gas inlet apertures 301a is the same as the number of the convergence channels 301b. In the embodiment, the number of the gas inlet apertures 301a and the convergence channels 301b is exemplified by four, but not limited thereto. The four gas inlet apertures 301a penetrate through the gas inlet plate 301 into the four convergence channels 301b respectively, and the four convergence channels 301b converge to the convergence chamber 301c.

Figure 3A:
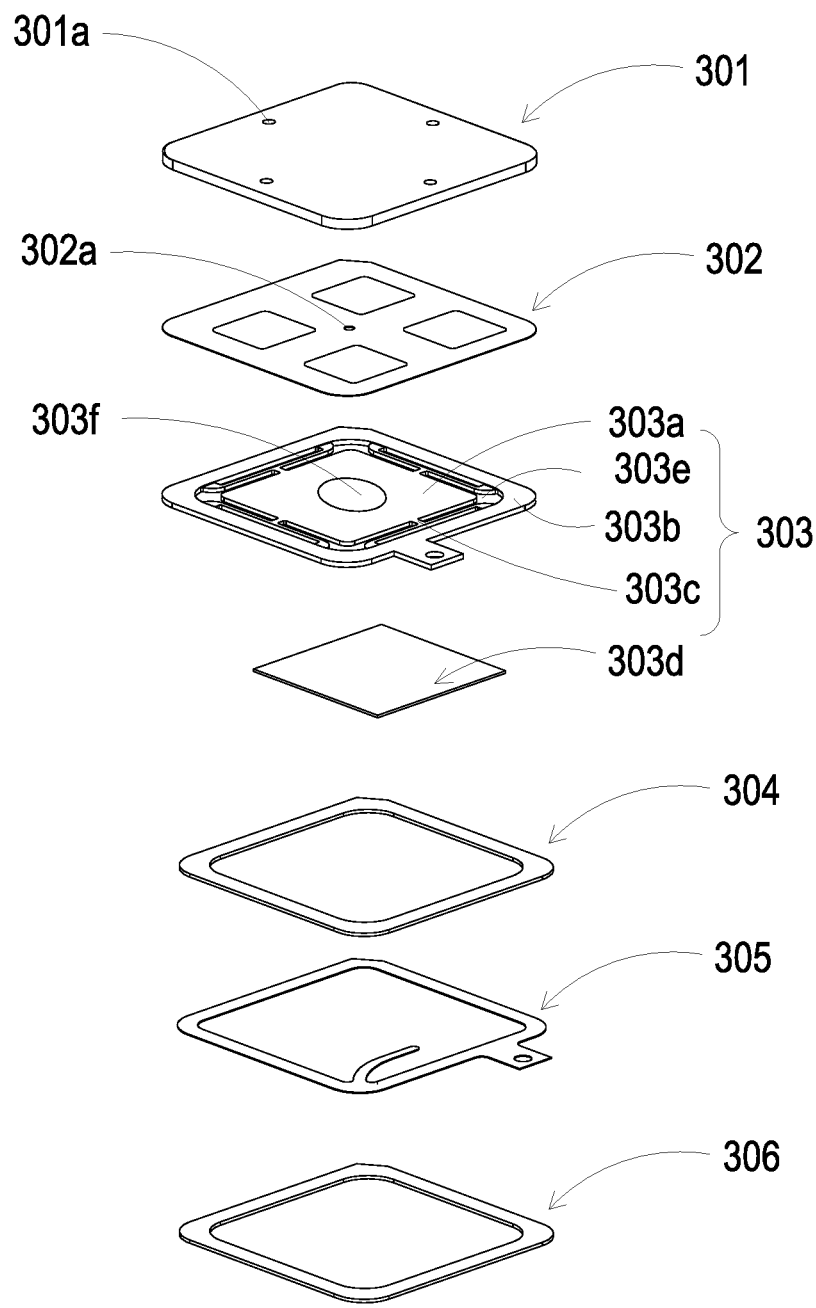
FIG. 3A is a schematic exploded view illustrating the related components of the actuating pump of the miniature gas detection and purification device according to the embodiment of the present disclosure and taken from a front perspective.
Figure 3B:
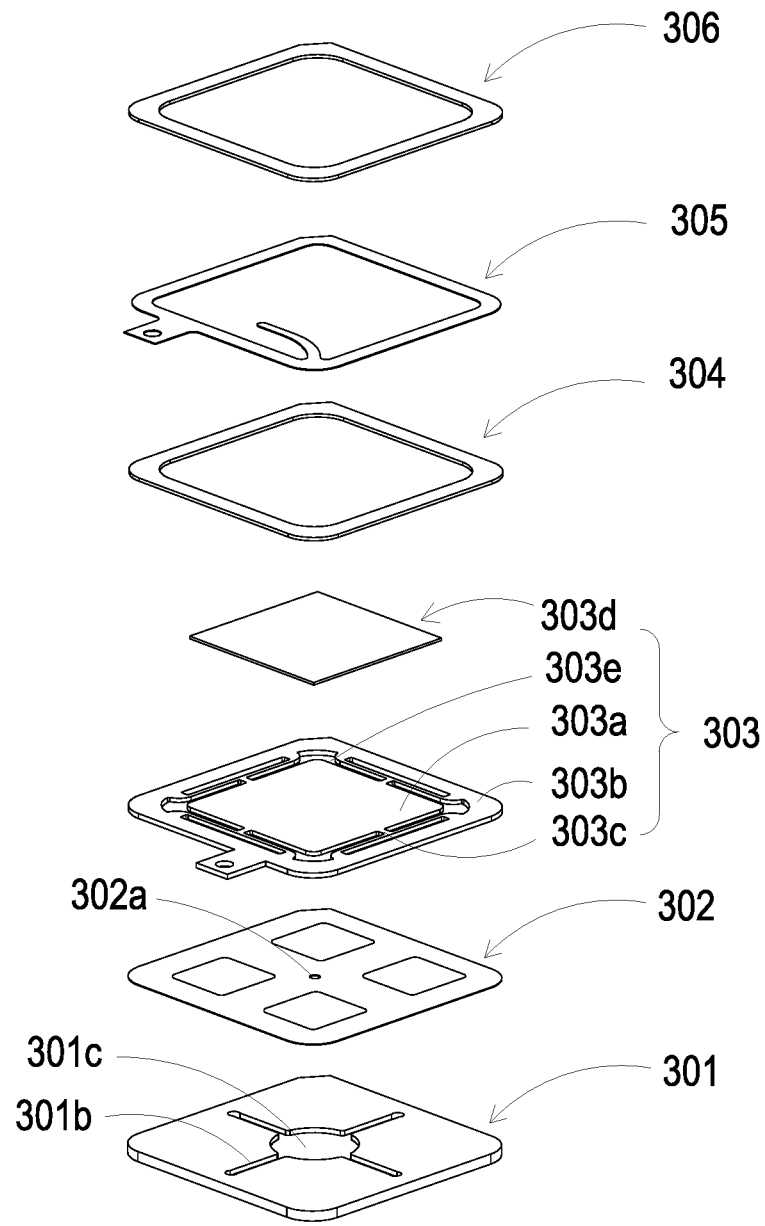
FIG. 3B is a schematic exploded view illustrating the related components of the actuating pump of the miniature gas detection and purification device according to the embodiment of the present disclosure and from a rear perspective.
Figure 4A:
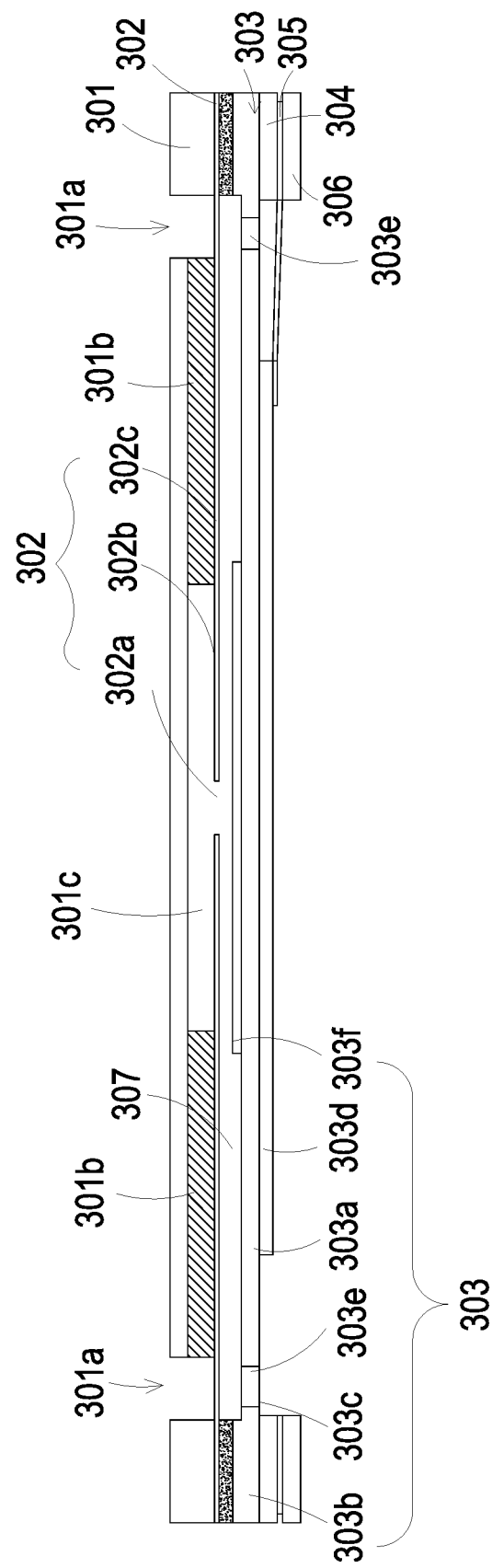
FIG. 4A is a schematic cross-sectional view illustrating the actuating pump of the miniature gas detection and purification device according to an embodiment of the present disclosure.

Please refer to FIGS. 3A, 3B and 4A. The resonance plate 302 is attached on the gas inlet plate 301. The resonance plate 302 has a central aperture 302a, a movable part 302b and a fixed part 302c. The central aperture 302a is located at a center of the resonance plate 302 and is corresponding to the convergence chamber 301c of the gas inlet plate 301. The movable part 302b surrounds the central aperture 302a and is corresponding to the convergence chamber 301c. The fixed part 302c is disposed around the periphery of the resonance plate 302 and securely attached on the gas inlet plate 301.

Please refer to FIGS. 3A, 3B and 4A, again. The piezoelectric actuator 303 includes a suspension plate 303a, an outer frame 303b, at least one bracket 303c, a piezoelectric element 303d, at least one clearance 303e and a bulge 303f. The suspension plate 303a is square-shaped because the square suspension plate 303a is more power-saving than the circular suspension plate. Generally, the consumed power of the capacitive load operated at the resonance frequency would induce as the resonance frequency raised. Since the resonance frequency of the square suspension plate 303a is obviously lower than that of the circular square suspension plate, the consumed power of the square suspension plate 303a would be fewer. Therefore, the square suspension plate 303a in the embodiment has the advantage of power-saving. In the embodiment, the outer frame 303b is disposed around the periphery of the suspension plate 303a, and at least one bracket 303c is connected between the suspension plate 303a and the outer frame 303b for elastically supporting the suspension plate 303a. The piezoelectric element 303d has a side, and the length of the side of the piezoelectric element 303d is less than or equal to that of the suspension plate 303a. The piezoelectric element 303d is attached on a surface of the suspension plate 303a. When a voltage is applied to the piezoelectric element 303d, the suspension plate 303a is driven to undergo the bending vibration. The at least one clearance 303e is formed between the suspension plate 303a, the outer frame 303b and the at least one bracket 303c for allowing the gas to flow through. The bulge 303f is formed on a surface of the suspension plate 303a opposite to the surface of the suspension plate 303a attached on the piezoelectric element 303d. In the embodiment, the bulge 303f is formed by using an etching process on the suspension plate 303a. Accordingly, the bulge 303f of the suspension plate 303a is integrally formed and protrudes from the surface opposite to that attached on the piezoelectric element 303d, and formed a convex structure.

Please refer to FIGS. 3A, 3B and 4A. In the embodiment, the gas inlet plate 301, the resonance plate 302, the piezoelectric actuator 303, the first insulation plate 304, the conducting plate 305 and the second insulation plate 306 are stacked and assembled sequentially. A chamber space 307 is formed between the suspension plate 303a and the resonance plate 302, and the chamber space 307 can be formed by filling a gap between the resonance plate 302 and the outer frame 303b of the piezoelectric actuator 303 with a material, such as a conductive adhesive, but not limited thereto. Thus, a specific depth between the resonance plate 302 and the suspension plate 303a is maintained to guide the gas to pass rapidly. In addition, since the resonance plate 302 and the suspension plate 303a are maintained at a suitable distance, the contact interference therebetween can reduced and the generated noise is largely reduced. In other embodiments, the thickness of the conductive adhesive filled into the gap between the resonance plate 302 and the outer frame 303b of the piezoelectric actuator 303 can be reduced by increasing the height of the outer frame 303b of the piezoelectric actuator 303. Therefore, the entire assembling structure of actuating pump 30 would not be indirectly influenced by the hot-pressing temperature and the cooling temperature, and avoiding the actual distance between the suspension plate 303a and the resonance plate 302 of the chamber space 307 being affected by the thermal expansion and contraction of the filling material of the conductive adhesive, but is not limited thereto. In addition, since the transportation effect of the actuating pump 30 is affected by the chamber space 307, it is very important to maintain a constant chamber space 307, so as to provide a stable transportation efficiency of the actuating pump 30.

Figure 4B:
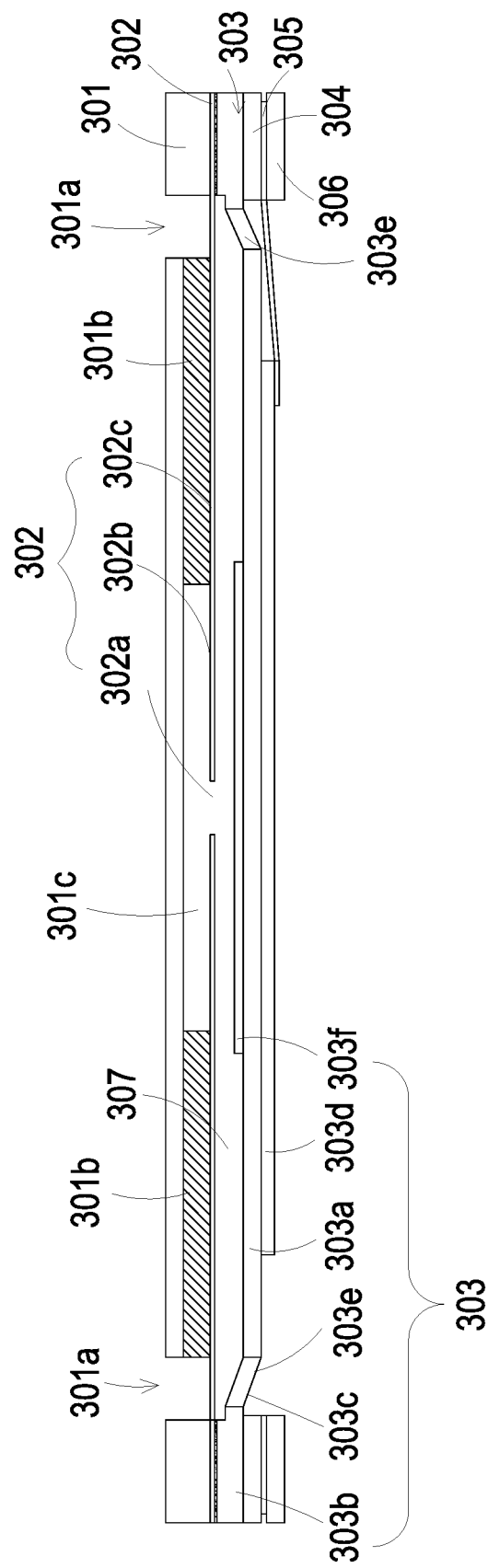
FIG. 4B is a schematic cross-sectional view illustrating the actuating pump of the miniature gas detection and purification device according to another embodiment of the present disclosure.

Please refer to FIG. 4B, in some other embodiments of the piezoelectric actuator 303, the suspension plate 303a is formed by stamping to make it extend at a distance in a direction away from the resonance plates 302. The extended distance can be adjusted through the at least one bracket 303c formed between the suspension plate 303a and the outer frame 303b. Consequently, the surface of the bulge 303f disposed on the suspension plate 303a and the surface of the outer frame 303b are non-coplanar. The piezoelectric actuator 303 is attached to the fixed part 302c of the resonance plate 302 by hot pressing a small amount of filling materials, such as a conductive adhesive, applied to the coupling surface of the outer frame 303b, thereby assembling the piezoelectric actuator 303 and the resonance plates 302 in combination. Therefore, the structure improvement of the chamber space 307 which is formed by directly stamping the suspension plate 303a of the piezoelectric actuator 303 as described above, the required modification of the chamber space 307 can be achieved by adjusting the stamping distance of the suspension plate 303a of the piezoelectric actuator 303. This can effectively simplify the structural design of the chamber space 307, and also achieves the advantages of simplifying the process and shortening the processing time. In addition, the first insulating plate 304, the conducting plate 305 and the second insulating plate 306 are all thin frame-shaped sheets, but are not limited thereto, and are sequentially stacked on the piezoelectric actuator 303 to form the entire structure of actuating pump 30.

Figure 4C:
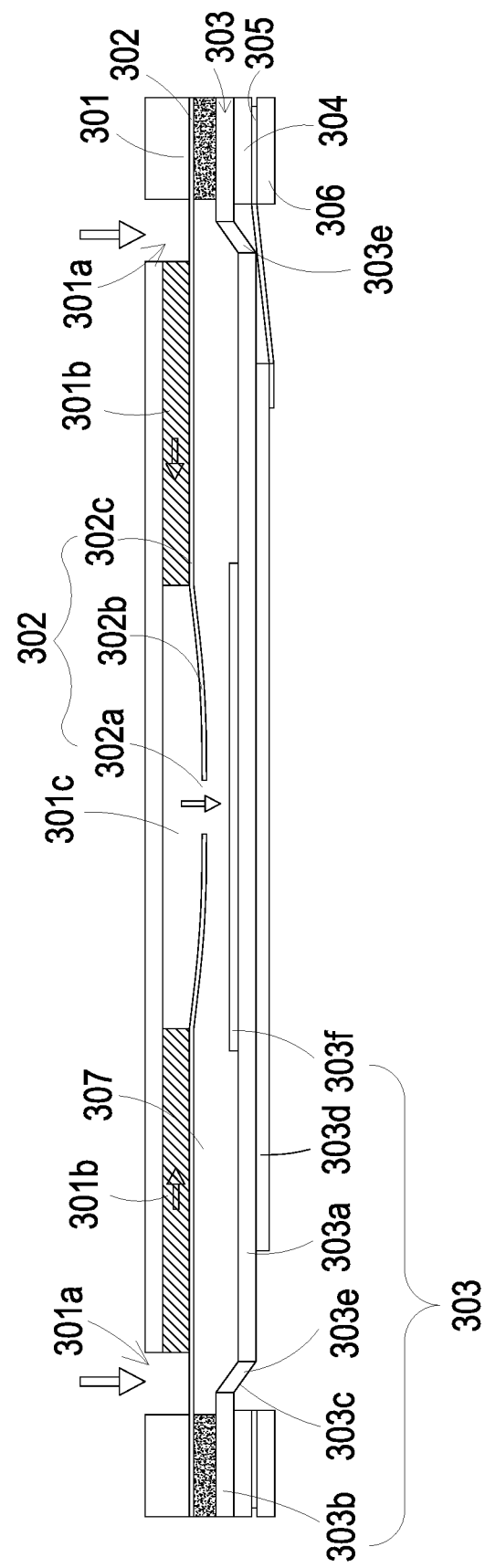
FIGS. 4C to 4E schematically illustrate the actions of the actuating pump of FIG. 4A.
Figure 4D:
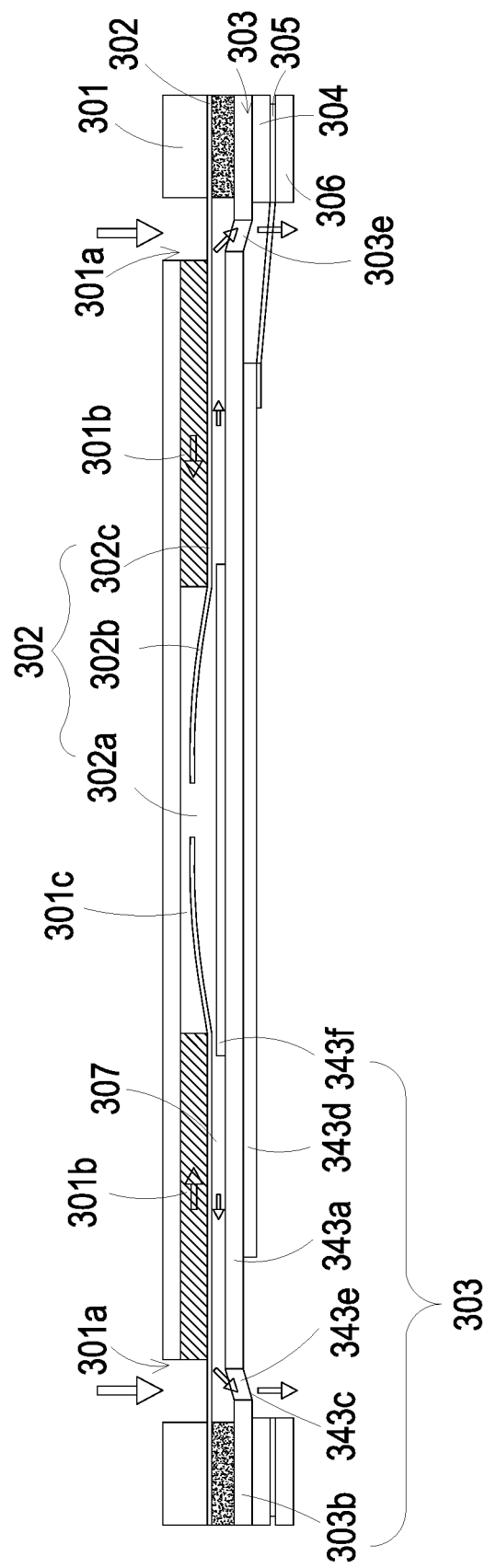
Figure 4E:
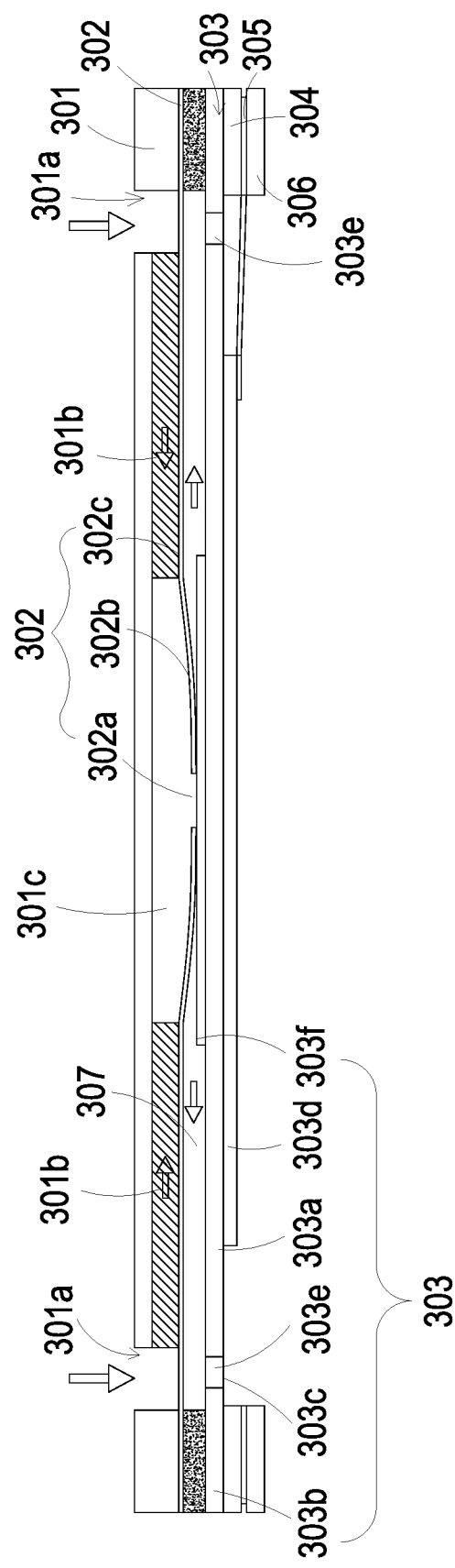

In order to understand the actuations of the actuating pump 30, please refer to FIGS. 4C to 4E. Please refer to FIG. 4C first, when the piezoelectric element 303d of the piezoelectric actuator 303 is deformed in response to an applied voltage, the suspension plate 303a is driven to displace in the direction away from the resonance plate 302. In that, the volume of the chamber space 307 is increased, a negative pressure is formed in the chamber space 307, and the gas in the convergence chamber 301c is introduced into the chamber space 307. At the same time, the resonance plate 302 is in resonance and is thus displaced synchronously, and thereby, increased the volume of the convergence chamber 301c. Since the gas in the convergence chamber 301c is introduced into the chamber space 307, the convergence chamber 301c is also result in a negative pressure state, and the gas is inhaled into the convergence chamber 301c through the gas inlet apertures 301a and the convergence channels 301b. Then, as shown in FIG. 4D, the piezoelectric element 303d drives the suspension plate 303a to displace toward the resonance plate 302 to compress the chamber space 307. Similarly, the resonance plate 302 is actuated and displaced away from the suspension plate 303a in resonance to the suspension plate 303a, and compress the air in the chamber space 307. Thus, the gas in the chamber space 307 is further transmitted downwardly to pass through the clearances 303e and achieves the effect of gas transportation. Finally, as shown in FIG. 4E, when the suspension plate 303a resiliently move back to an initial state, the resonance plate 302 displaces toward the suspension plate 303a due to its inertia momentum, and keep on pushes the gas in the chamber space 307 toward the clearances 303e, and the volume of the convergence chamber 301c is increased at the same time. Thus, the gas outside can be continuously inhaled and passed through the gas inlet apertures 301a and the convergence channels 301b, and converged in the convergence chamber 301c. By repeating the actuations illustrated in FIGS. 4C to 4E continuously, the actuating pump 30 can continuously transport the gas at high speed. The gas enters the gas inlet apertures 301a, flows through a flow path formed by the gas inlet plate 301 and the resonance plate 3022 and result in a pressure gradient, and then transported through the clearances 303e, so as to achieve the operation of gas transporting of the actuating pump 30.

Please refer to FIG. 2A, FIG. 2B, FIG. 5D and FIG. 13. In the embodiment, the gas detection module is disposed in the main body 1, and spatially corresponding to the detecting inlet 14 and the detecting outlet 15 for detecting the gas surrounding in the environment of the user to obtain a gas detection datum. In the embodiment, the gas detection module 4 includes a control circuit board 4a, a gas detection main part 4b, a processor 4c, a communicator 4d and a battery unit 4e. In the embodiment, the battery unit 4e is electrically connected to the control circuit board 4a and provides an operating power to the gas detection main part 4b, so that the gas detection main part 4b is allowed to detect the gas introduced from the outside of the main body 1 to obtain the gas detection datum. Preferably but not exclusively, the battery unit 4e is externally electrically connected to a power supply device 5 through wired communication transmission or wireless communication transmission for charging. In the embodiment, the processor 4c receives the gas detection datum to calculate, process and control an enablement and a disablement of the gas guider 3 for purifying the gas, and the communicator 4d receives the gas detection datum from the processor 4c and externally transmits the gas detection datum to an external device 6. It allows the external device 6 to obtain an information in regard to the gas detection and generate an alarm indication. Preferably but not exclusively, the external device 6 is a mobile device or a cloud processing device.

Figure 5A:
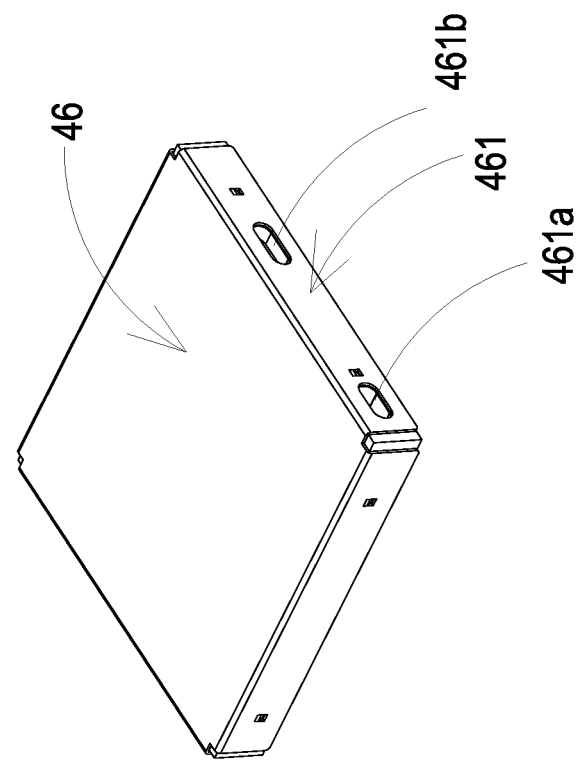
FIG. 5A is a schematic exterior view illustrating a gas detection main part according to an embodiment of the present disclosure.
Figure 5B:
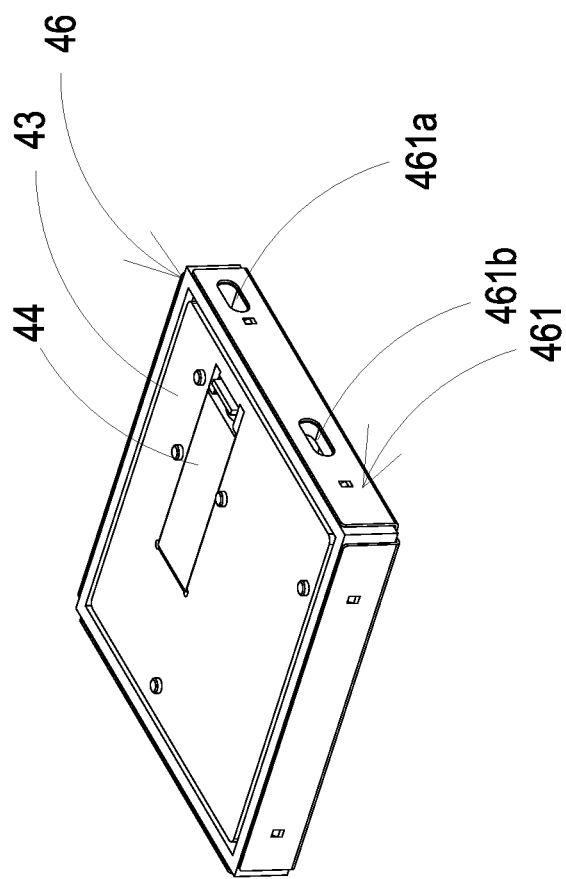
FIG. 5B is a schematic exterior view illustrating the gas detection main part according to the embodiment of the present disclosure and taken from another perspective angle.
Figure 5C:
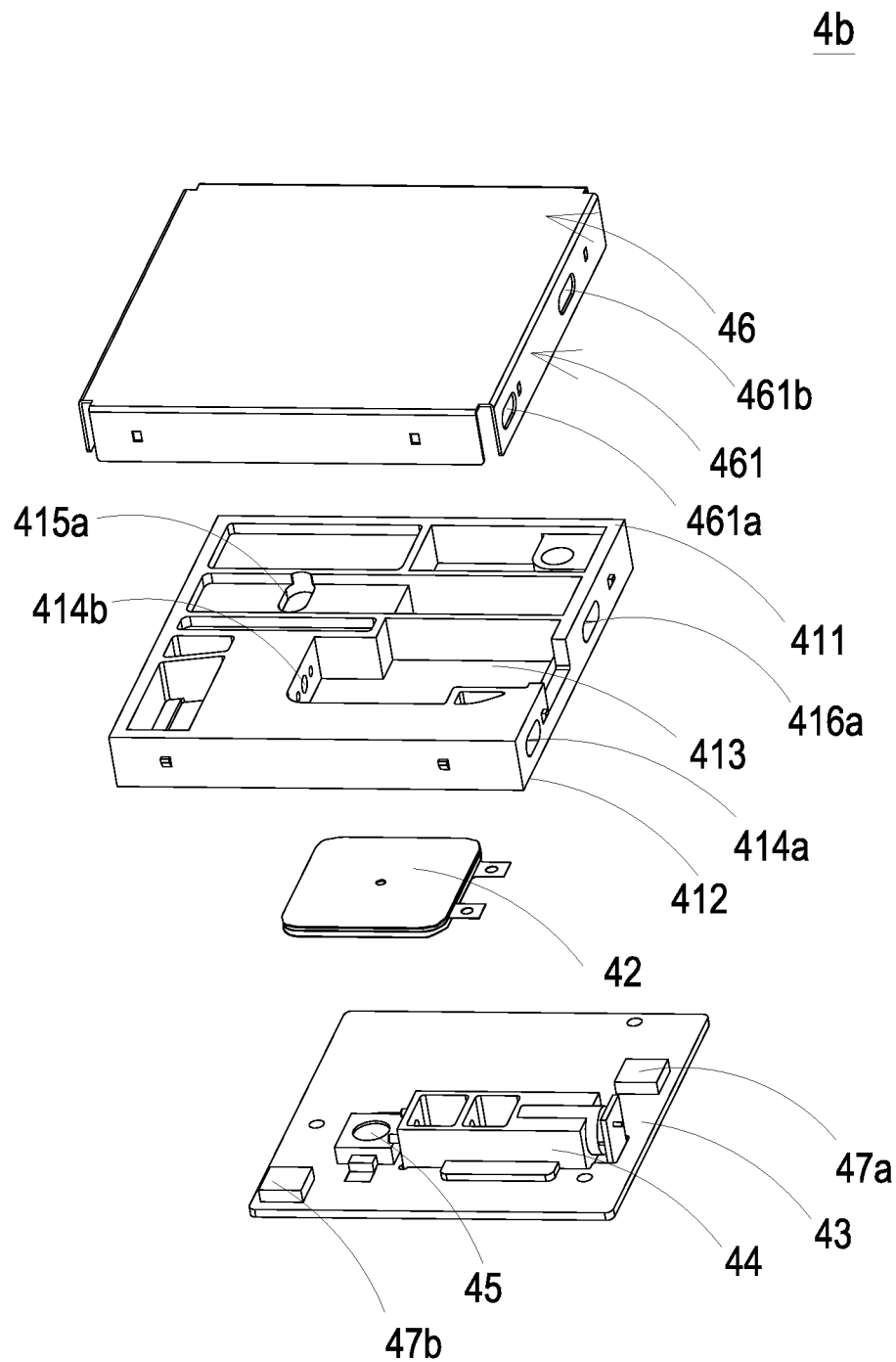
FIG. 5C is a schematic exploded view illustrating the gas detection main part of the present disclosure.
Figure 5D:
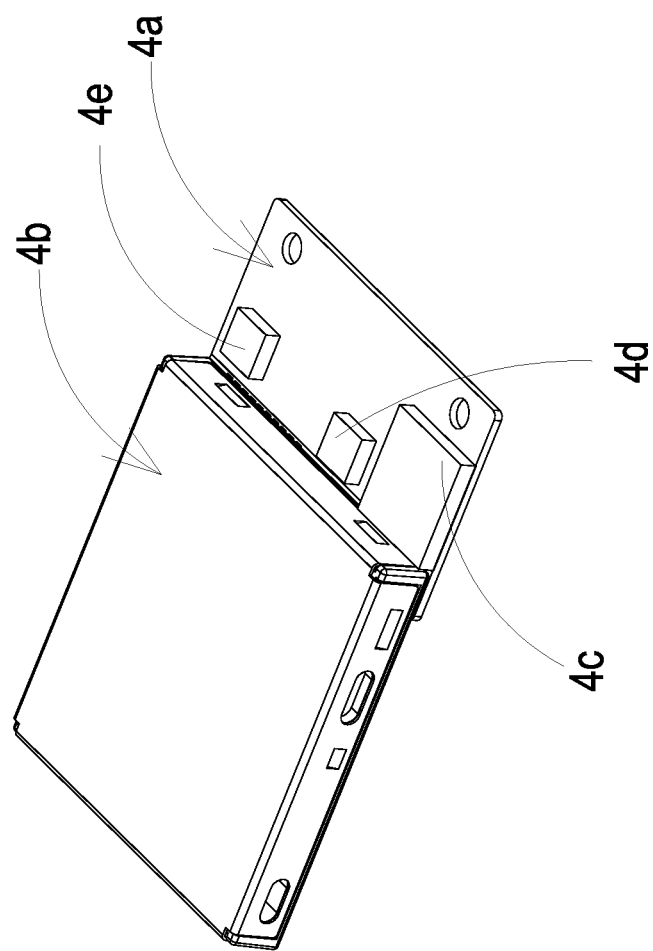
FIG. 5D is a schematic perspective view illustrating the relevant components of the gas detection module of the present disclosure.
Figure 6A:
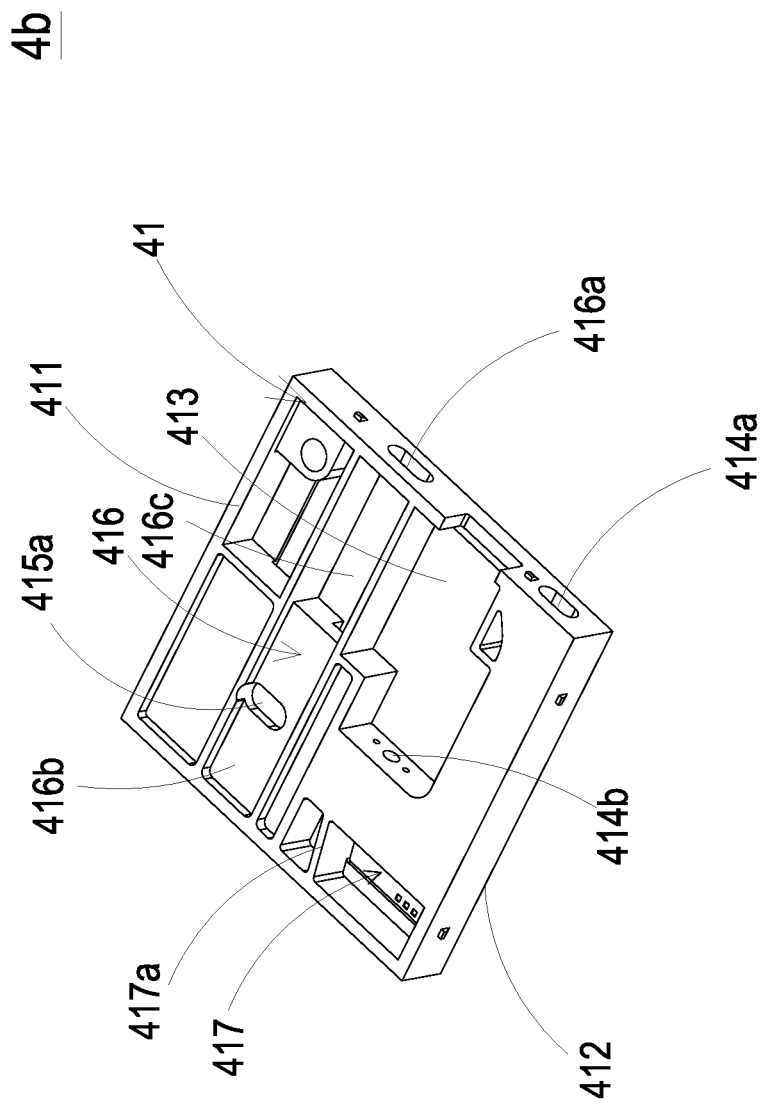
FIG. 6A is a schematic perspective view illustrating a base of the gas detection main part of the present disclosure.
Figure 6B:
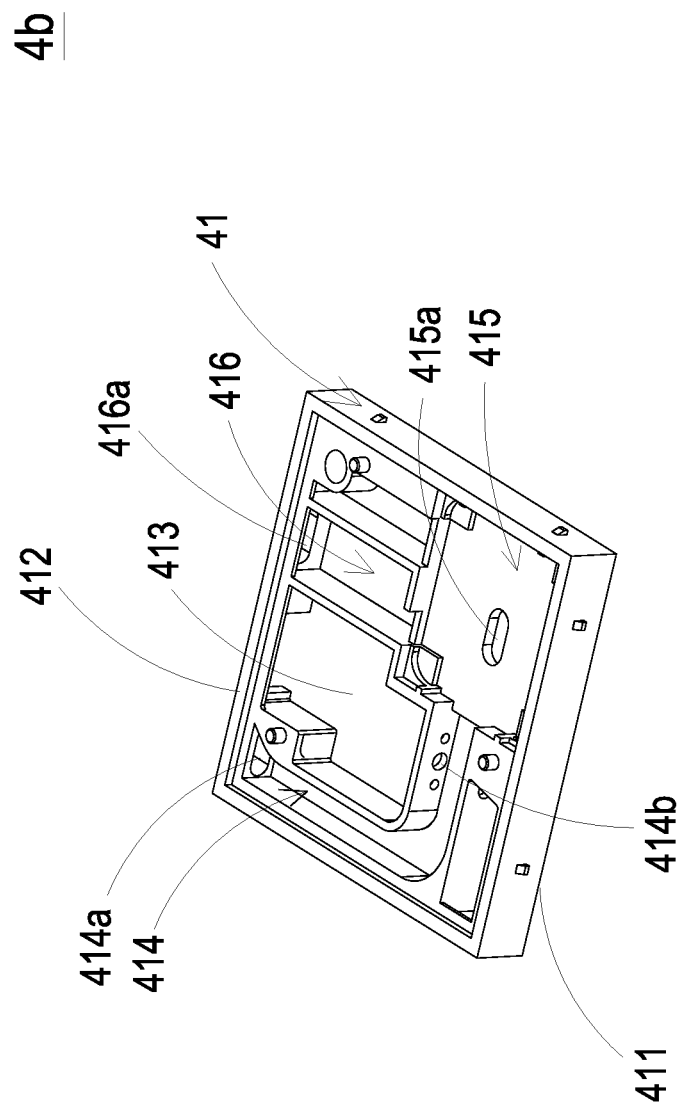
FIG. 6B is a schematic perspective view illustrating the base of the gas detection main part of the present disclosure and from another perspective angle.
Figure 7:
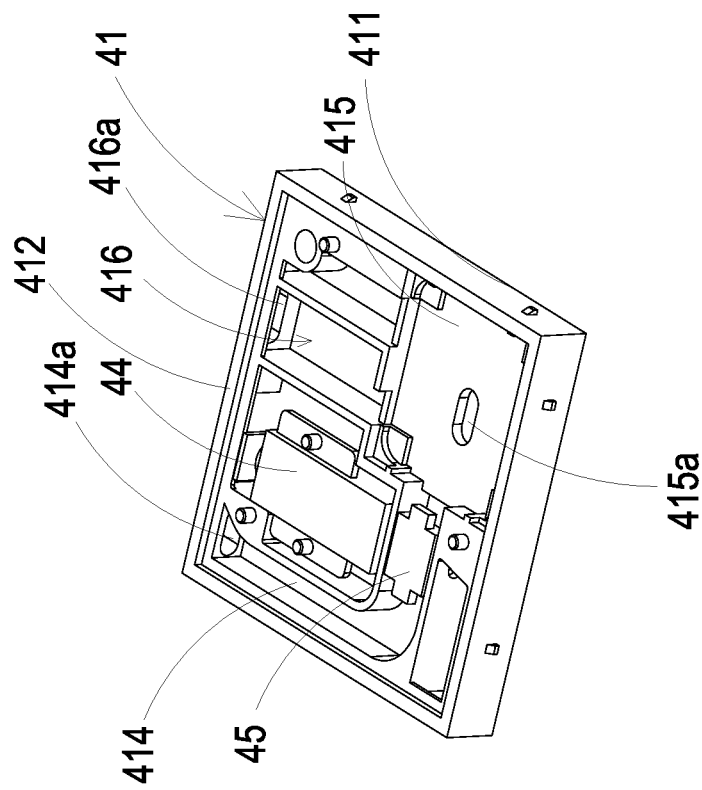
FIG. 7 is a schematic perspective view illustrating a laser component and a particulate sensor accommodated in the base of the present disclosure.
Figure 11A:
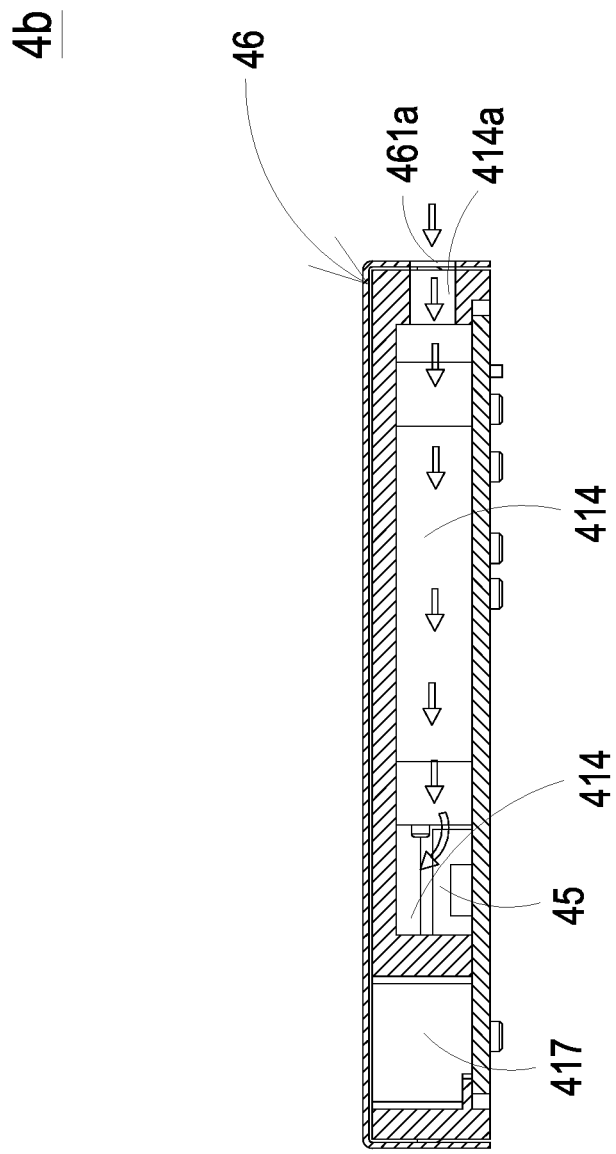
FIGS. 11A to 11C schematically illustrate gas flowing paths of the gas detection main part of the present disclosure.

Please refer to FIGS. 5A to 5C, FIGS. 6A to 6B, FIG. 7 and FIGS. 8A to 8B. In the embodiment, the gas detection main part 4b includes a base 41, a piezoelectric actuator 42, a driving circuit board 43, a laser component 44, a particulate sensor 45 and an outer cover 46. The base 41 includes a first surface 411, a second surface 412, a laser loading region 413, a gas-inlet groove 414, a gas-guiding-component loading region 415 and a gas-outlet groove 416. In the embodiment, the first surface 411 and the second surface 412 are two surfaces opposite to each other. In the embodiment, the laser loading region 413 is hollowed out from the first surface 411 to the second surface 412. The gas-inlet groove 414 is recessed from the second surface 412 and disposed adjacent to the laser loading region 413. The gas-inlet groove 414 includes a gas-inlet 414a and two lateral walls. The gas-inlet 414a is in fluid communication with an environment outside the base 41, and spatially corresponding to an inlet opening 461a of the outer cover 46. A transparent window 414b is opened on the two lateral walls and is in fluid communication with the laser loading region 413. Therefore, the first surface 411 of the base 41 is covered and attached by the outer cover 46, and the second surface 412 is covered and attached by the driving circuit board 43. Thus, the gas-inlet groove 414 defines a gas-inlet path, as shown in FIG. 7 and FIG. 11A.

Figure 11B:
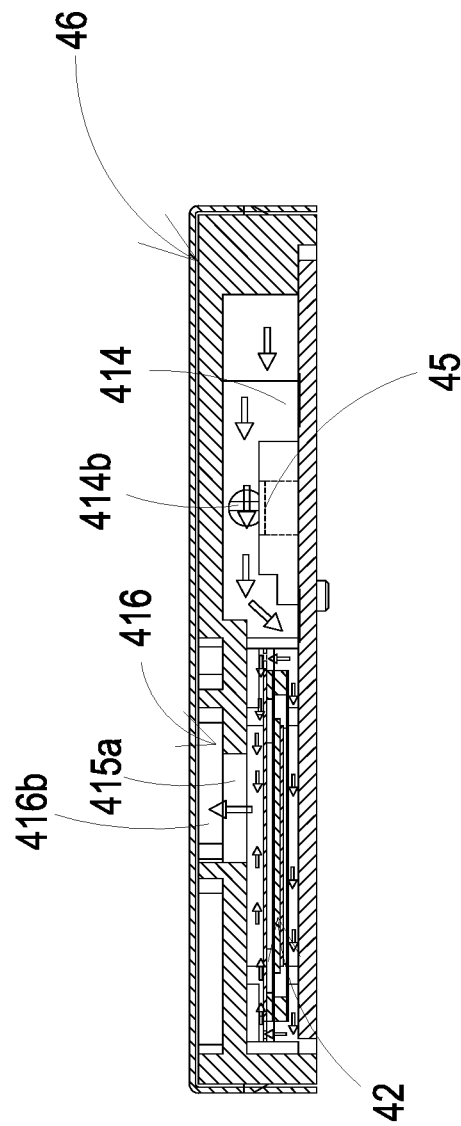
Figure 11C:
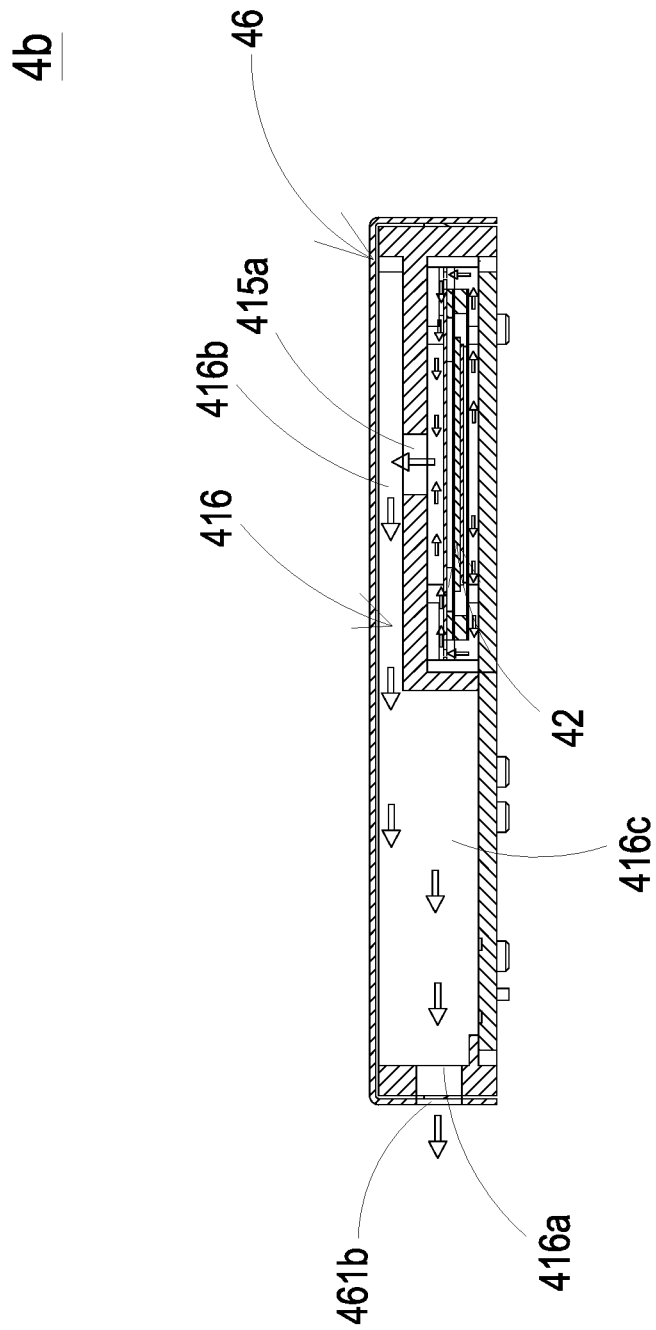

Please refer to FIGS. 6B and 6C. In the embodiment, the gas-guiding-component loading region 415 is recessed from the second surface 412 and in fluid communication with the gas-inlet groove 414. A ventilation hole 415a penetrates a bottom surface of the gas-guiding-component loading region 415. In the embodiment, the gas-outlet groove 416 includes a gas-outlet 416a, and the gas-outlet 416a is spatially corresponding to the outlet opening 461b of the outer cover 46. The gas-outlet groove 416 includes a first section 416b and a second section 416c. The first section 416b hollowed out from the first surface 411 is spatially corresponding to a vertical projection area of the gas-guiding-component loading region 415. The second section 416c is hollowed out from the first surface 411 to the second surface 412 in a region where the first surface 411 is not aligned with the vertical projection area of the gas-guiding-component loading region 415. The first section 416b and the second section 416c are connected to form a stepped structure. Moreover, the first section 416b of the gas-outlet groove 416 is in fluid communication with the ventilation hole 415a of the gas-guiding-component loading region 415, and the second section 416c of the gas-outlet groove 416 is in fluid communication with the gas-outlet 416a. In that, when the first surface 411 of the base 41 is attached and covered by the outer cover 46, and the second surface 412 of the base 41 is attached and covered by the driving circuit board 43, the gas-outlet groove 416 defines a gas-outlet path, as shown in FIGS. 7 and 11C.

Please refer to FIG. 5C and FIG. 7. In the embodiment, the laser component 44 and the particulate sensor 45 are disposed on the driving circuit board 43 and accommodated in the base 41. In order to describe the positions of the laser component 44 and the particulate sensor 45 in the base 41, the driving circuit board 43 is omitted in FIG. 7 for clarity. Please refer to FIG. 5C, FIG. 6B, FIG. 7 and FIG. 12. In the embodiment, the laser component 44 is accommodated in the laser loading region 413 of the base 41, and the particulate sensor 45 is accommodated in the gas-inlet groove 414 of the base 41 and aligned to the laser component 44. In addition, the laser component 44 is spatially corresponding to the transparent window 414b, a light beam emitted by the laser component 44 passes through the transparent window 414b and is irradiated into the gas-inlet groove 414. A light beam path emitted from the laser component 44 passes through the transparent window 414b and extends in a direction perpendicular to the gas-inlet groove 414. In the embodiment, a projecting light beam emitted from the laser component 44 passes through the transparent window 414b and enters the gas-inlet groove 414, and suspended particles contained in the gas passing through the gas-inlet groove 414 is irradiated by the projecting light beam. When the suspended particles contained in the gas are irradiated to generate scattered light spots, the scattered light spots are detected and calculated by the particulate sensor 45 for obtaining related information in regard to the sizes and the concentration of the suspended particles contained in the gas. The suspended particles contained in the gas includes bacteria and viruses. In the embodiment, the particulate sensor 45 is a PM2.5 sensor.

Figure 8A:
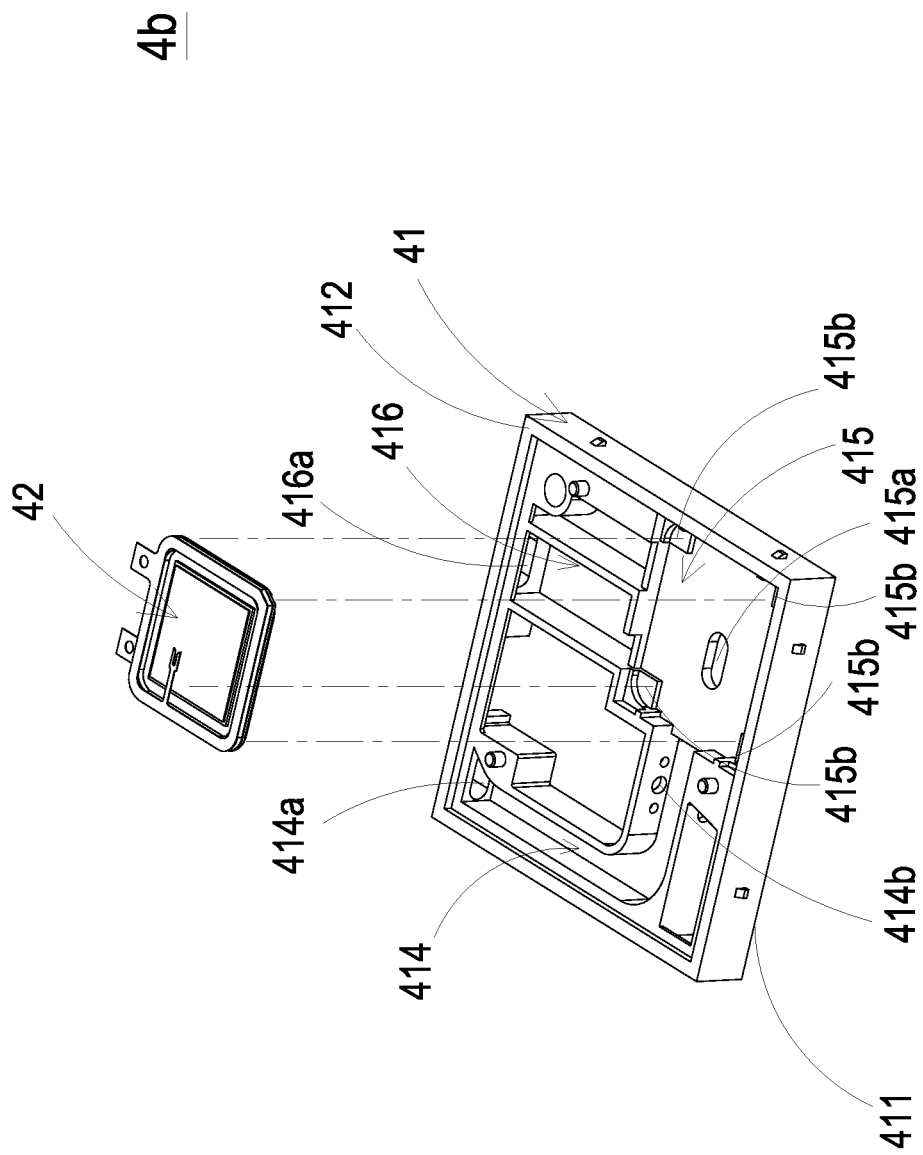
FIG. 8A is a schematic exploded view illustrating the combination of the piezoelectric actuator and the base according to the present disclosure.
Figure 8B:
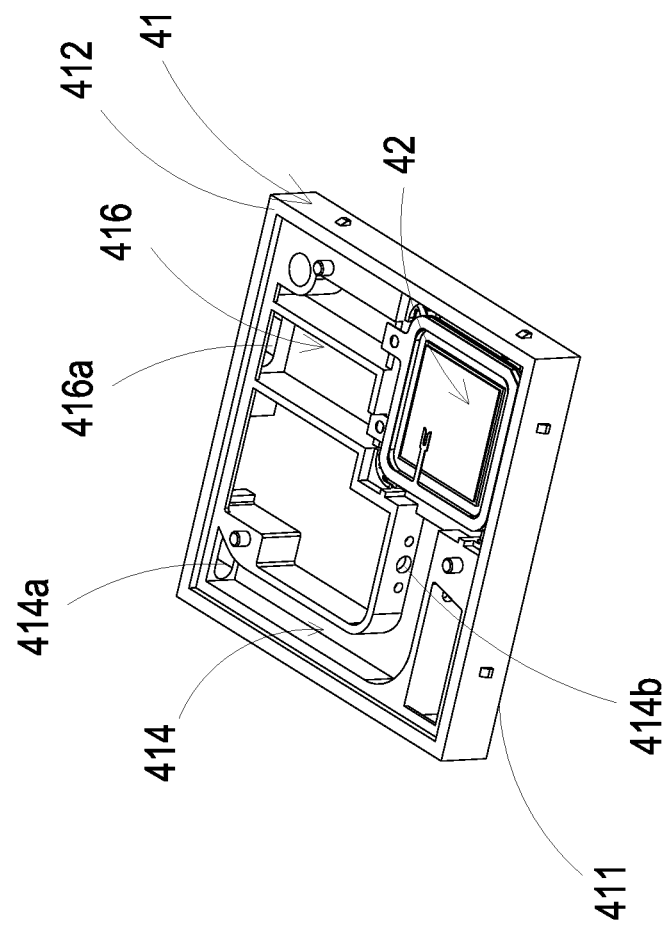
FIG. 8B is a schematic perspective view illustrating the combination of the piezoelectric actuator and the base according to the present disclosure.

Please refer to FIG. 8A and FIG. 8B. The piezoelectric actuator 42 is accommodated in the gas-guiding-component loading region 415 of the base 41. Preferably but not exclusively, the gas-guiding-component loading region 415 is square and includes four positioning protrusions 415b disposed at four corners of the gas-guiding-component loading region 415, respectively. The piezoelectric actuator 42 is disposed in the gas-guiding-component loading region 415 through the four positioning protrusions 415b. In addition, as shown in FIGS. 6A, 6B, 11B and 11C, the gas-guiding-component loading region 415 is in fluid communication with the gas-inlet groove 414. When the piezoelectric actuator 42 is enabled, the gas in the gas-inlet groove 414 is inhaled by the piezoelectric actuator 42, so that the gas flows into the piezoelectric actuator 42. Thereafter, the gas is transported into the gas-outlet groove 416 through the ventilation hole 415a of the gas-guiding-component loading region 415.

Please refer to FIGS. 5B and 5C. In the embodiment, the driving circuit board 43 covers and is attached to the second surface 412 of the base 41, and the laser component 44 is positioned and disposed on the driving circuit board 43, and is electrically connected to the driving circuit board 43. The particulate sensor 45 is positioned and disposed on the driving circuit board 43, and is electrically connected to the driving circuit board 43. Preferably but not exclusively, the particulate sensor 25 is disposed at an orthogonal position where the gas-inlet groove 214 intersects with the light beam path of the laser component 24. The outer cover 46 covers the base 41 and is attached to the first surface 411 of the base 41. Moreover, the outer cover 46 includes a side plate 461. The side plate 461 has an inlet opening 461a and an outlet opening 461b. When the outer cover 46 covers the base 41, the inlet opening 461a is spatially corresponding to the gas-inlet 414a of the base 41 (as shown in FIG. 11A), and the outlet opening 461b is spatially corresponding to the gas-outlet 416a of the base 41 (as shown in FIG. 11C).

Figure 9A:
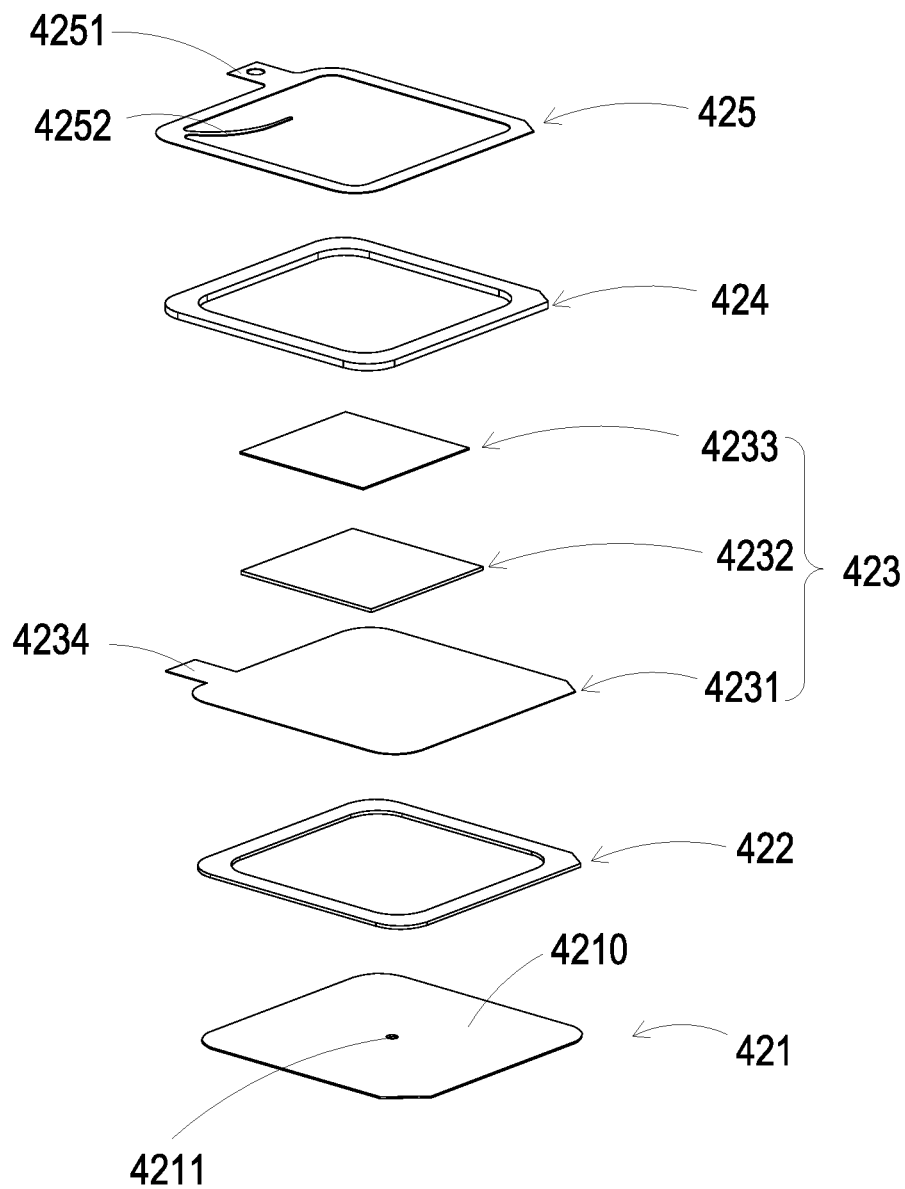
FIG. 9A is a schematic exploded view illustrating the piezoelectric actuator of the present disclosure.
Figure 9B:
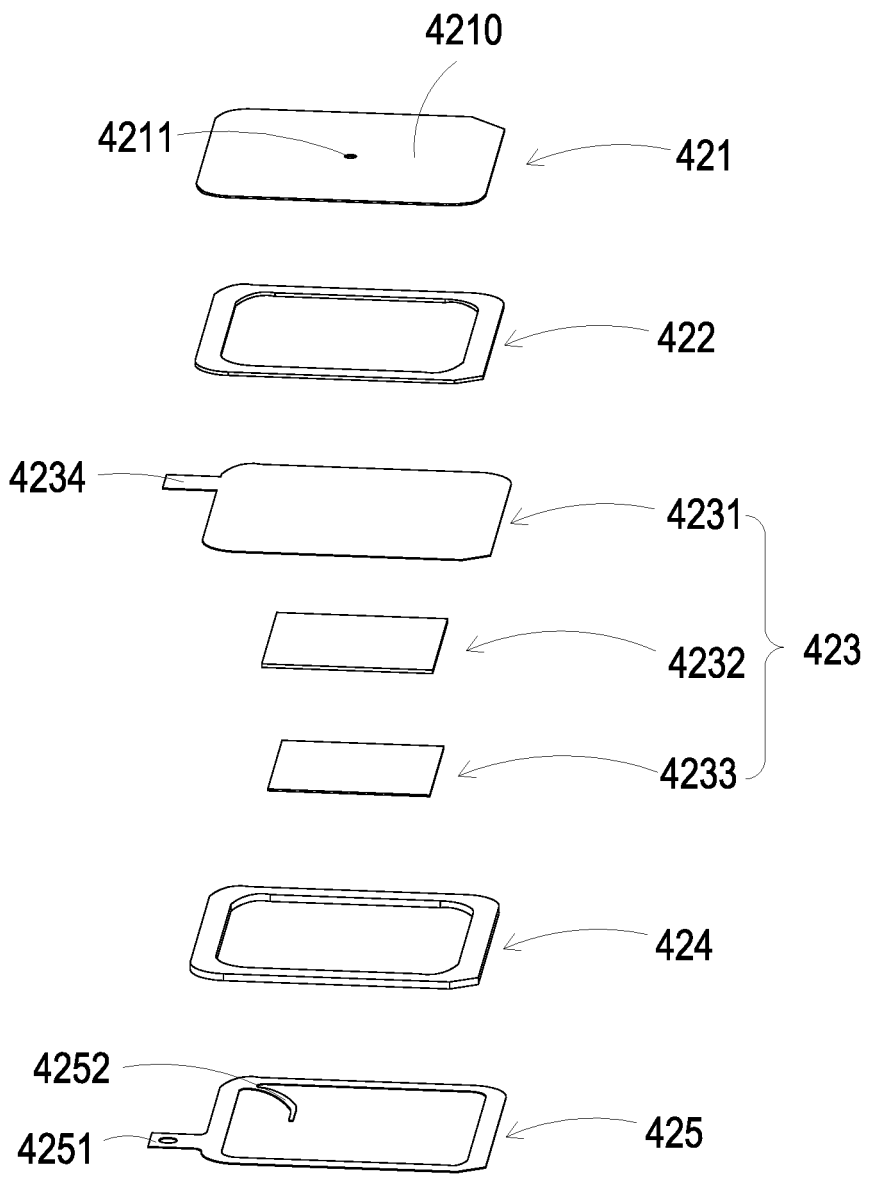
FIG. 9B is a schematic exploded view illustrating the piezoelectric actuator of the present disclosure and taken from another perspective angle.

Please refer to FIGS. 9A and 9B. In the embodiment, the piezoelectric actuator 42 includes a gas-injection plate 421, a chamber frame 422, an actuator element 423, an insulation frame 424 and a conductive frame 425. In the embodiment, the gas-injection plate 421 is made by a flexible material and includes a suspension plate 4210 and a hollow aperture 4211. The suspension plate 4210 is a sheet structure and permitted to undergo a bending deformation. Preferably but not exclusively, the shape and the size of the suspension plate 4210 are corresponding to an inner edge of the gas-guiding-component loading region 415. The shape of the suspension plate 4210 is one selected from the group consisting of a square, a circle, an ellipse, a triangle and a polygon. The hollow aperture 4211 passes through a center of the suspension plate 4210, so as to allow the gas to flow through.

In the embodiment, the chamber frame 422 is carried and stacked on the gas-injection plate 421. In addition, the shape of the chamber frame 422 is corresponding to the gas-injection plate 421. The actuator element 423 is carried and stacked on the chamber frame 422. A resonance chamber 426 is collaboratively defined by the actuator element 423, the chamber frame 422 and the suspension plate 4210 and formed between the actuator element 423, the chamber frame 422 and the suspension plate 4210. The insulation frame 424 is carried and stacked on the actuator element 423 and the appearance of the insulation frame 424 is similar to that of the chamber frame 422. The conductive frame 425 is carried and stacked on the insulation frame 424, and the appearance of the conductive frame 425 is similar to that of the insulation frame 424. In addition, the conductive frame 425 includes a conducting pin 4251 and a conducting electrode 4252. The conducting pin 4251 is extended outwardly from an outer edge of the conductive frame 425, and the conducting electrode 4252 is extended inwardly from an inner edge of the conductive frame 425. Moreover, the actuator element 423 further includes a piezoelectric carrying plate 4231, an adjusting resonance plate 4232 and a piezoelectric plate 4233. The piezoelectric carrying plate 4231 is carried and stacked on the chamber frame 422. The adjusting resonance plate 4232 is carried and stacked on the piezoelectric carrying plate 4231. The piezoelectric plate 4233 is carried and stacked on the adjusting resonance plate 4232. The adjusting resonance plate 4232 and the piezoelectric plate 4233 are accommodated in the insulation frame 424. The conducting electrode 4252 of the conductive frame 425 is electrically connected to the piezoelectric plate 4233. In the embodiment, the piezoelectric carrying plate 4231 and the adjusting resonance plate 4232 are made by a conductive material. The piezoelectric carrying plate 4231 includes a piezoelectric pin 4234. The piezoelectric pin 4234 and the conducting pin 4251 are electrically connected to a driving circuit (not shown) of the driving circuit board 43, so as to receive a driving signal, such as a driving frequency and a driving voltage. In that, an electric circuit for the driving signal is formed by the piezoelectric pin 4234, the piezoelectric carrying plate 4231, the adjusting resonance plate 4232, the piezoelectric plate 4233, the conducting electrode 4252, the conductive frame 425 and the conducting pin 4251. Moreover, the insulation frame 424 is insulated between the conductive frame 425 and the actuator element 423, so as to avoid the occurrence of a short circuit. Thereby, the driving signal is transmitted to the piezoelectric plate 4233. After receiving the driving signal such as the driving frequency and the driving voltage, the piezoelectric plate 4233 deforms due to the piezoelectric effect, and the piezoelectric carrying plate 4231 and the adjusting resonance plate 4232 are further driven to generate the bending deformation in the reciprocating manner.

As described above, the adjusting resonance plate 4232 is located between the piezoelectric plate 4233 and the piezoelectric carrying plate 4231 and served as a buffer between the piezoelectric plate 4233 and the piezoelectric carrying plate 4231. Thereby, the vibration frequency of the piezoelectric carrying plate 4231 is adjustable. Basically, the thickness of the adjusting resonance plate 4232 is greater than the thickness of the piezoelectric carrying plate 4231, and the thickness of the adjusting resonance plate 4232 is adjustable, thereby adjusting the vibration frequency of the actuator element 423.

Figure 10A:
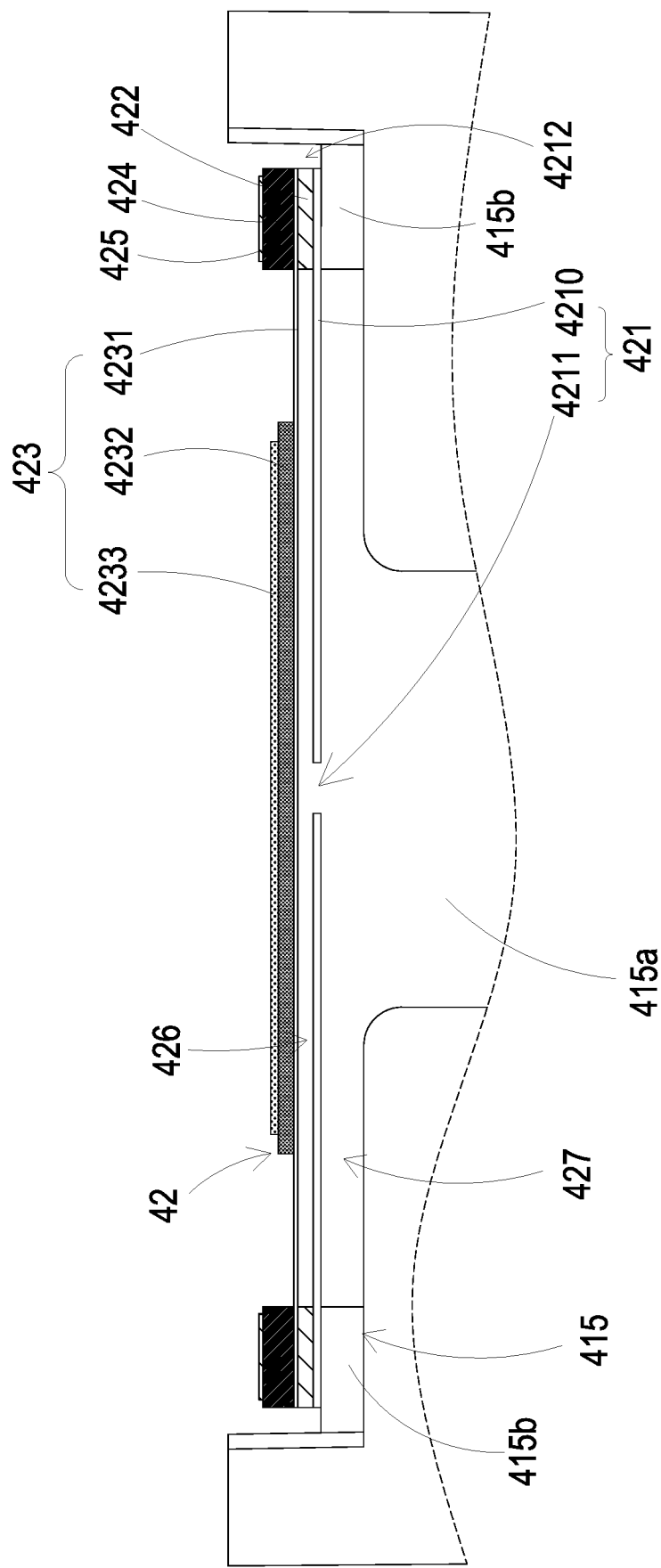
FIG. 10A is a schematic cross-sectional view illustrating the piezoelectric actuator accommodated in the gas-guiding-component loading region according to the present disclosure.

Please refer to FIG. 9A, FIG. 9B and FIG. 10A. In the embodiment, the gas-injection plate 421, the chamber frame 422, the actuator element 423, the insulation frame 424 and the conductive frame 425 are stacked and positioned in the gas-guiding-component loading region 415 sequentially, so that the piezoelectric actuator 42 is supported and positioned in the gas-guiding-component loading region 415. The bottom of the gas-injection plate 421 is fixed on the four positioning protrusions 415b of the gas-guiding-component loading region 415 for supporting and positioning, so that the suspension plate 4210 of the gas-injection plate 421 and an inner edge of the gas-guiding-component loading region 415 define a plurality of clearances 4212 in the piezoelectric actuator 42 for gas flowing.

Please refer to FIG. 10A. A flowing chamber 427 is formed between the gas-injection plate 421 and the bottom surface of the gas-guiding-component loading region 415. The flowing chamber 427 is in fluid communication with the resonance chamber 426 between the actuator element 423, the chamber frame 422 and the suspension plate 4210 through the hollow aperture 4211 of the gas-injection plate 421. Through controlling the vibration frequency of the gas in the resonance chamber 426 and making it close to the vibration frequency of the suspension plate 4210, the Helmholtz resonance effect is induced between the resonance chamber 426 and the suspension plate 4210, and thereby improves the efficiency of gas transportation.

Figure 10B:
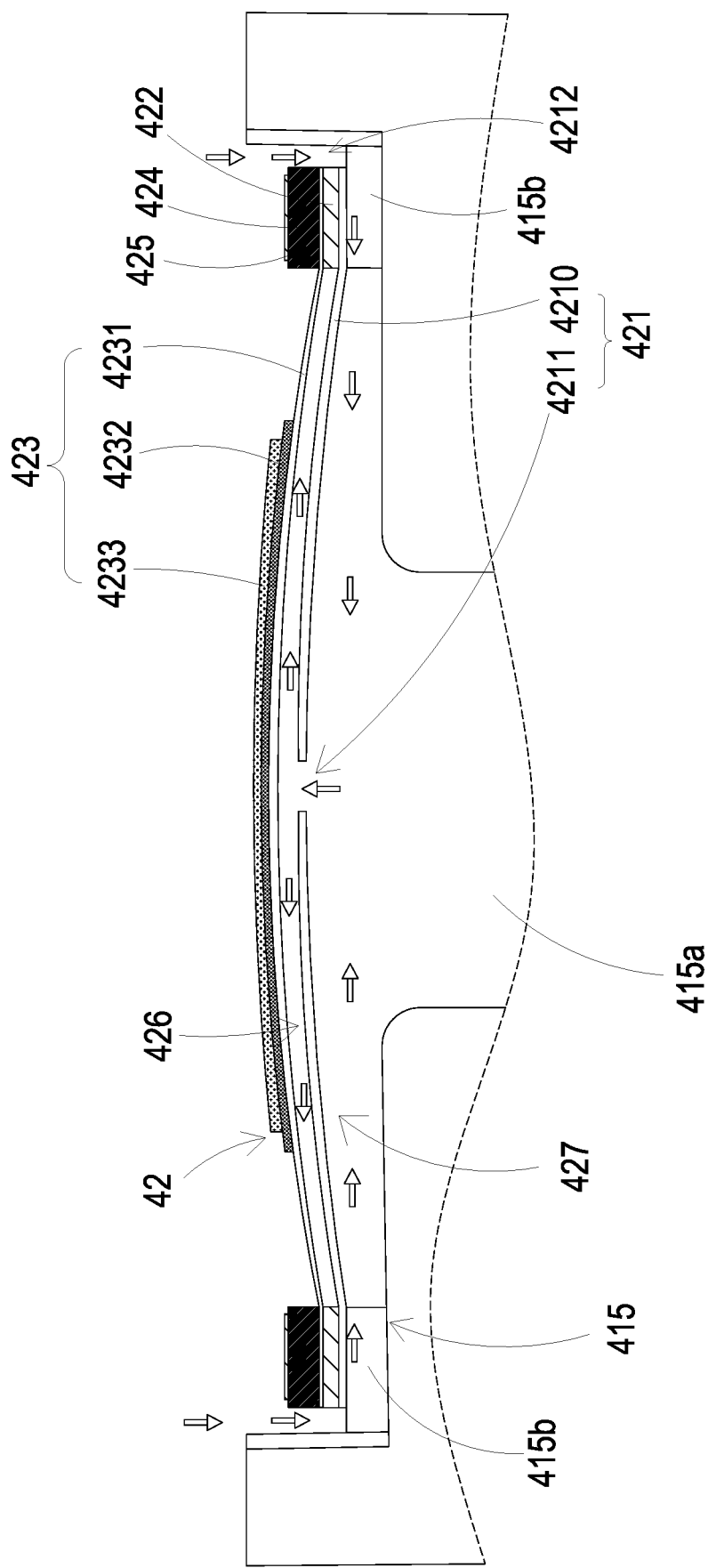
FIGS. 10B and 10C schematically illustrate the actions of the piezoelectric actuator of FIG. 10A.
Figure 10C:
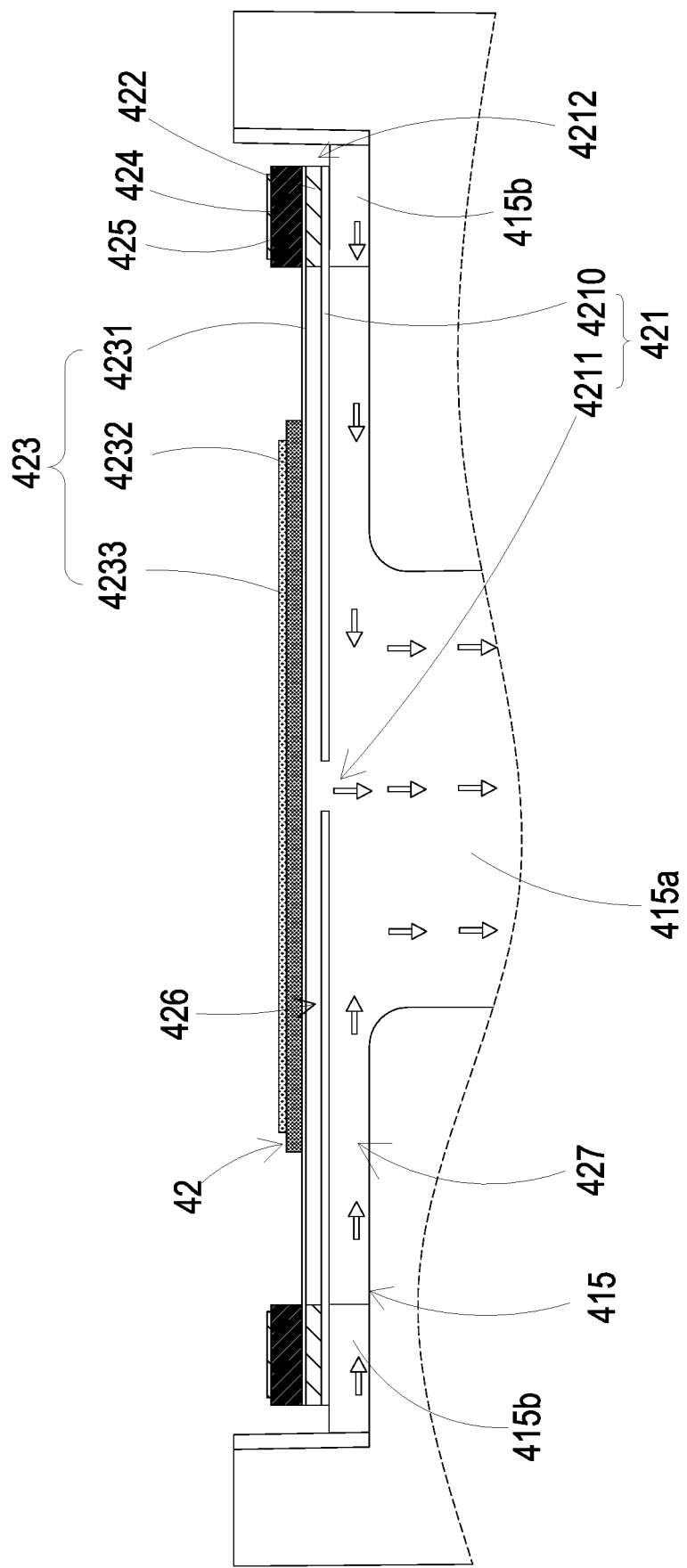

Please refer to FIG. 10B. When the piezoelectric plate 4233 is moved away from the bottom surface of the gas-guiding-component loading region 415, the suspension plate 4210 of the gas-injection plate 421 is driven to move away from the bottom surface of the gas-guiding-component loading region 415 by the piezoelectric plate 4233. In that, the volume of the flowing chamber 427 is expanded rapidly, the internal pressure of the flowing chamber 427 is decreased to form a negative pressure, and the gas outside the piezoelectric actuator 42 is inhaled through the clearances 4212 and enters the resonance chamber 426 through the hollow aperture 4211. Consequently, the pressure in the resonance chamber 426 is increased to generate a pressure gradient. Further as shown in FIG. 10C, when the suspension plate 4210 of the gas-injection plate 421 is driven by the piezoelectric plate 4233 to move towards the bottom surface of the gas-guiding-component loading region 415, the gas in the resonance chamber 426 is discharged out rapidly through the hollow aperture 4211, and the gas in the flowing chamber 427 is compressed. In that, the converged gas is quickly and massively ejected out of the flowing chamber 427 in a gas state close to an ideal gas state of the Benulli's law, and transported to the ventilation hole 415a of the gas-guiding-component loading region 415. By repeating the above actions shown in FIG. 10B and FIG. 10C, the piezoelectric plate 4233 is driven to generate the bending deformation in a reciprocating manner. According to the principle of inertia, the gas pressure inside the resonance chamber 426 after exhausting is lower than the equilibrium gas pressure outside, and the gas is introduced into the resonance chamber 426 again. Moreover, the vibration frequency of the gas in the resonance chamber 426 is controlled to be close to the vibration frequency of the piezoelectric plate 4233, so as to generate the Helmholtz resonance effect and to achieve the gas transportation at high speed and in large quantities.

Furthermore, as shown in FIG. 11A, the gas is inhaled through the inlet opening 461a of the outer cover 46, flows into the gas-inlet groove 414 of the base 41 through the gas-inlet 414a, and is transported to the position of the particulate sensor 45. Further as shown in FIG. 11B, the piezoelectric actuator 42 is enabled continuously to inhale the gas in the gas-inlet path, so as to facilitate the gas to be introduced and transported above the particulate sensor 45 rapidly and stably. At this time, a projecting light beam emitted from the laser component 44 passes through the transparent window 414b to irritate the suspended particles contained in the gas flowing above the particulate sensor 45 in the gas-inlet groove 414. When the suspended particles contained in the gas are irradiated to generate scattered light spots, the scattered light spots are detected and calculated by the particulate sensor 45 for obtaining related information in regard to the sizes and the concentration of the suspended particles contained in the gas. Furthermore, the gas above the particle sensor 45 is continuously driven and transported by the piezoelectric actuator 42, flows into the ventilation hole 415a of the gas-guiding-component loading region 415, and is transported to the first section 416b of the gas-outlet groove 416. As shown in FIG. 11C, after the gas flows into the first section 416b of the gas-outlet groove 416, the gas is continuously transported into the first section 416b by the piezoelectric actuator 42, and the gas in the first section 416b is pushed to the second section 416c. Finally, the gas is discharged out through the gas-outlet 416a and the outlet opening 461b.

Figure 12:
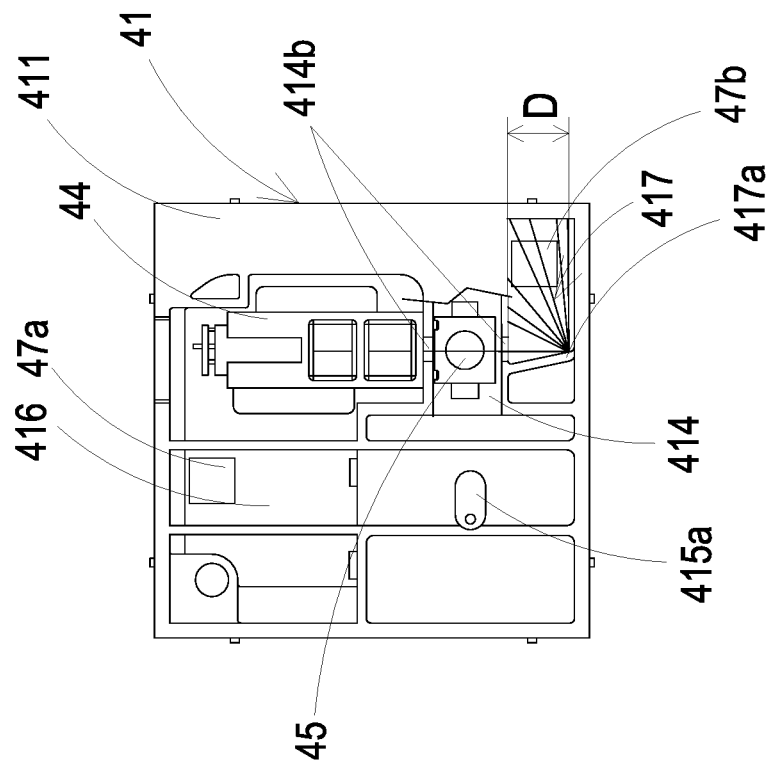
FIG. 12 schematically illustrates a light beam path emitted from the laser component of the gas detection main body of the present disclosure.
Figure 13:
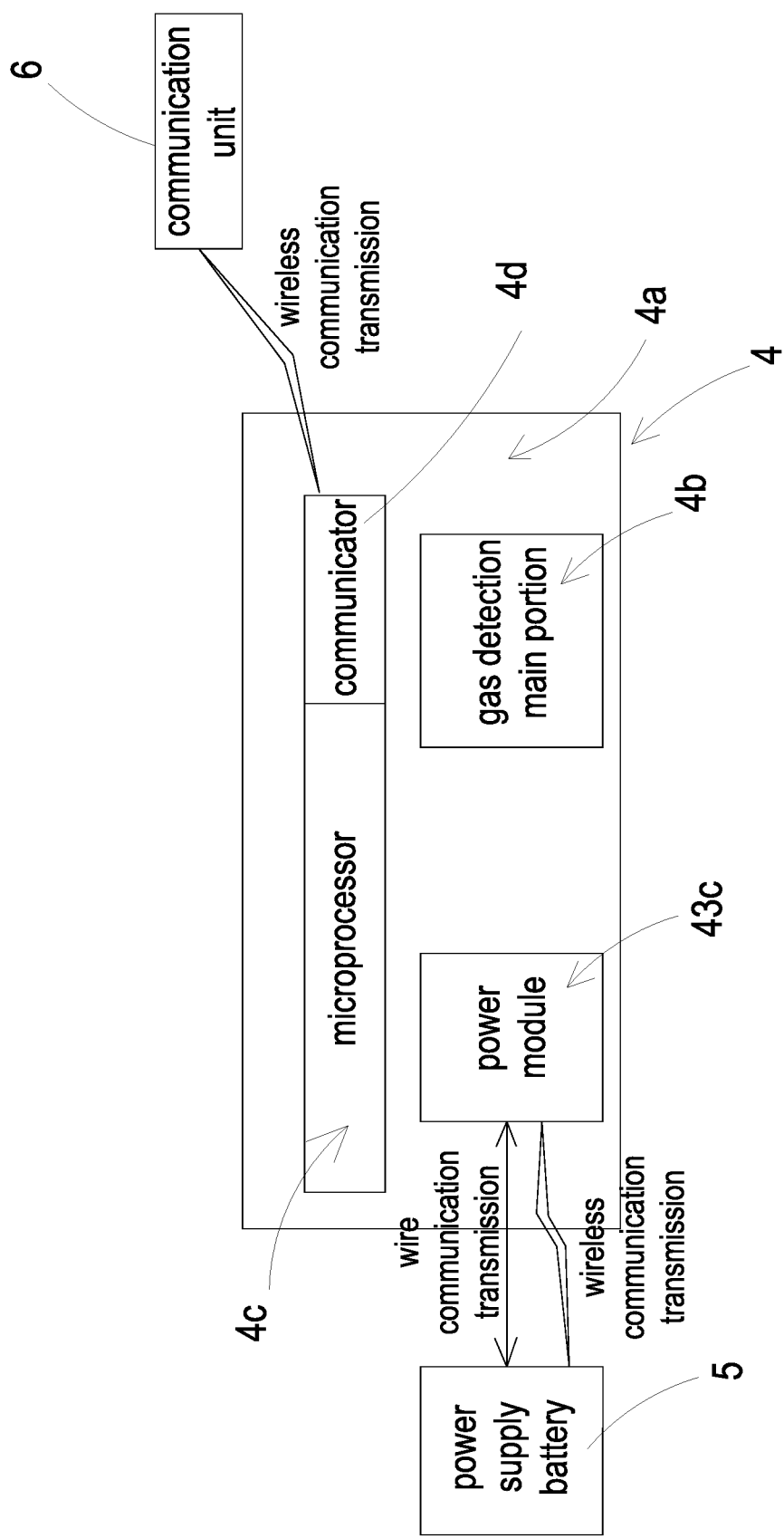
FIG. 13 a block diagram illustrating a configuration of a control circuit unit and the related components of the miniature gas detection and purification device according to an embodiment of the present disclosure.

As shown in FIG. 12, the base 41 further includes a light trapping region 417. The light trapping region 417 is hollowed out from the first surface 411 to the second surface 412 and spatially corresponding to the laser loading region 413. In the embodiment, the light trapping region 417 is corresponding to the transparent window 414b so that the light beam emitted by the laser component 44 is projected into the light trapping region 417. The light trapping region 417 includes a light trapping structure 417a having an oblique cone surface. The light trapping structure 417a is spatially corresponding to the light beam path emitted from the laser component 44. In addition, the projecting light beam emitted from the laser component 44 is reflected into the light trapping region 417 through the oblique cone surface of the light trapping structure 417a. It prevents the projecting light beam from being reflected to the position of the particulate sensor 45. In the embodiment, a light trapping distance D is maintained between the transparent window 414b and a position where the light trapping structure 417a receives the projecting light beam. Preferably but not exclusively, the light trapping distance D is greater than 3 mm. When the light trapping distance D is less than 3 mm, the projecting light beam projected on the light trapping structure 417a could be easily reflected back to the position of the particulate sensor 45 directly due to excessive stray light generated after reflection, and resulted in distortion of detection accuracy.

Please refer to FIG. 5C and FIG. 12. The gas detection main part 4b of the gas detection module 4 in the present disclosure can not only detect the suspended particles in the gas, but also detect the characteristics of the introduced gas. Preferably but not exclusively, the gas can be detected is at least one selected from the group consisting of formaldehyde, ammonia, carbon monoxide, carbon dioxide, oxygen, ozone and a combination thereof. In the embodiment, the gas detection main part 4b of the gas detection module 4 further includes a first volatile-organic-compound sensor 47a. The first volatile-organic-compound sensor 47a is positioned and disposed on the driving circuit board 43, electrically connected to the driving circuit board 43, and accommodated in the gas-outlet groove 416, so as to detect the gas flowing through the gas-outlet path of the gas-outlet groove 416. Thus, the concentration or the characteristics of volatile organic compounds contained in the gas in the gas-outlet path is detected. Alternatively, in an embodiment, the gas detection main part 4b of the gas detection module 4 further includes a second volatile-organic-compound sensor 47b. The second volatile-organic-compound sensor 47b is positioned and disposed on the driving circuit board 43, and electrically connected to the driving circuit board 43. In the embodiment, the second volatile-organic-compound sensor 47*b* is accommodated in the light trapping region 417. Thus, the concentration or the characteristics of volatile organic compounds contained in the gas flowing through the gas-inlet path of the gas-inlet groove 414 and transported into the light trapping region 417 through the transparent window 414*b* is detected.

According to the above description, the present disclosure provides the miniature gas detection and purification device based on the gas detection main part 4*b* of the gas detection module 4 detecting the gas detection datum, the processor 4*c* receiving the gas detection datum to calculate, process and control the enablement and a disablement of the gas guider 3 for purifying the gas, and the communicator 4*d* receiving the gas detection datum from the processor 4*c* and externally transmitting the gas detection datum to the external device 6, it allows the external device 6 to obtain an information in regard to the gas detection and generate an alarm indication. Furthermore, with the gas guider 3 performing the actuation operation, the gas of the environment surrounding the user is inhaled through the inlet 11 and flows through the purification module 2 for filtration and purification. Finally, the benefit of guiding the purified gas to a region close to the user is achieved. Preferably but not exclusively, the region close to the user has a volume of 50 cm in length×50 cm in width×50 cm in height, so that the user can breathe the clean and purified gas. In that, the miniature gas detection and purification device of the present disclosure for the user to carry with himself is achieved. It is capable of solving the air quality problem of the user's surrounding environment in real time.

In summary, the present disclosure provides a miniature gas detection and purification device for a user to carry with himself. The miniature gas detection and purification device includes a main body, a purification module, a gas guider and a gas detection module. The gas detection module detects gas of the environment surrounding the user to obtain a gas detection datum, for controlling the gas guider to perform the actuation operations. Thereby, the gas of the environment surrounding the user is introduced into the main body and flows through the purification module for filtration and purification. Finally, the benefit of guiding the purified gas to a region close to the user is achieved. It is helpful of solving the air quality problem of the user's surrounding environment in real time. The present disclosure fulfills the requirements of industrial applicability and inventive steps.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A gas detection and purification device, comprising:
    a main body comprising at least one inlet, at least one outlet, a detecting inlet, a detecting outlet and a gas-flow channel, wherein the gas-flow channel is disposed between the at least one inlet and the at least one outlet;
    a purification module disposed in the gas-flow channel of the main body and comprising a filter screen;
    a gas guider disposed in the gas-flow channel of the main body and located at a side of the purification module, wherein gas is inhaled by the gas guider through the at least one inlet, flows through the purification module for filtration and purification, and is discharged out through the at least one outlet; and
    a gas detection module disposed in the main body, spatially corresponding to the detecting inlet and the detecting outlet, and comprising a gas detection main part, a processor, a communicator and a battery unit, wherein the battery unit provides an operating power to the gas detection main part, the gas detection main part detects a gas introduced from the outside of the main body through the detecting inlet to obtain a gas detection datum, the processor receives the gas detection datum to calculate, process and control an enablement and a disablement of the gas guider, and the communicator receives the gas detection datum from the processor;
    wherein the processor controls operations of the gas guider in the enablement according to the gas detection datum detected by the gas detection module, so that the gas is inhaled through the at least one inlet and flows through the purification module for filtration and purification, and the purified gas is guided to a region from which a user draws breath and discharged from the at least one outlet;
    wherein the gas detection main part comprises:
        a base comprising:
            a first surface;
            a second surface opposite to the first surface;
            a laser loading region hollowed out from the first surface to the second surface;
            a gas-inlet groove recessed from the second surface and disposed adjacent to the laser loading region, wherein the gas-inlet groove comprises a gas-inlet and two lateral walls, and a transparent window is opened on one of the two lateral walls and is in fluid communication with the laser loading region; and
        an outer cover covering the first surface of the base and comprising a side plate, wherein the side plate has an inlet opening spatially corresponding to the gas-inlet and an outlet opening spatially corresponding to a gas-outlet of a gas-outlet groove recessed from the first surface of the base.

2. The gas detection and purification device according to claim 1, wherein the gas introduced is filtered through the filter screen for filtration and purification.

3. The gas detection and purification device according to claim 2, wherein the filter screen is one selected from the group consisting of an electrostatic filter screen, an activated carbon filter screen and a high efficiency particulate air filter screen.

4. The gas detection and purification device according to claim 2, wherein the filter screen is coated with a layer of a cleansing factor containing chlorine dioxide to inhibit viruses and bacteria in the gas.

5. The gas detection and purification device according to claim 2, wherein the filter screen is coated with an herbal protective layer consisting of *Rhus chinensis* Mill extracts from Japan and *Ginkgo biloba* extracts to form an herbal protective anti-allergic filter.

6. The gas detection and purification device according to claim 2, wherein the filter screen is coated with a silver ion to inhibit viruses and bacteria in the gas.

7. The gas detection and purification device according to claim 2, wherein the filter screen consists of a high efficiency particulate air filter screen and an electrostatic filter screen and is used to filter viruses and bacteria in the air.

8. The gas detection and purification device according to claim 2, wherein the filter screen is a module consisting of a high efficiency particulate air filter screen and one selected from the group consisting of a photo-catalyst, a voltage plasma, a negative ionizer and an ultraviolet lamp, and is used to filter or decompose viruses and bacteria in the air.

9. The gas detection and purification device according to claim 1, wherein the gas guider is a fan.

10. The gas detection and purification device according to claim 1, wherein the gas guider is an actuating pump, and the actuating pump comprises:
 a gas inlet plate having at least one gas inlet aperture, at least one convergence channel and a convergence chamber, wherein the at least one gas inlet aperture is disposed to inhale the gas, the at least one gas inlet aperture correspondingly penetrates through the gas inlet plate and in fluid communication with the at least one convergence channel, and the at least one convergence channel converges with the convergence chamber, so that the gas inhaled through the at least one gas inlet aperture is converged into the convergence chamber;
 a resonance plate disposed on the gas inlet plate and having a central aperture, a movable part and a fixed part, wherein the central aperture is disposed at a center of the resonance plate, and corresponds to the center of the convergence chamber of the gas inlet plate, the movable part surrounds the central aperture and corresponds to the convergence chamber, and the fixed part surrounds the movable part and is fixedly attached on the gas inlet plate; and
 a piezoelectric actuator correspondingly disposed on the resonance plate;
 wherein a chamber space is formed between the resonance plate and the piezoelectric actuator, so that when the piezoelectric actuator is driven, the gas introduced from the at least one gas inlet aperture of the gas inlet plate is converged to the convergence chamber through the at least one convergence channel, and flows through the central aperture of the resonance plate so as to produce a resonance by the movable part of the resonance plate and the piezoelectric actuator to transport the gas.

11. The gas detection and purification device according to claim 10, wherein the piezoelectric actuator comprises:
 a suspension plate being square-shaped and being permitted to undergo a bending vibration;
 an outer frame surrounding the suspension plate;
 at least one bracket connected between the suspension plate and the outer frame to provide an elastic support for the suspension plate; and
 a piezoelectric element having a side, wherein a length of the side of the piezoelectric element is less than or equal to a side of the suspension plate, and the piezoelectric element is attached on a surface of the suspension plate, wherein when a voltage is applied to the piezoelectric element, the suspension plate is driven to undergo the bending vibration.

12. The gas detection and purification device according to claim 10, wherein the piezoelectric actuator comprises:
 a suspension plate being square-shaped and being permitted to undergo a bending vibration;
 an outer frame surrounding the suspension plate;
 at least one bracket connected and formed between the suspension plate and the outer frame to provide an elastic support for the suspension plate, wherein a surface of the suspension plate and a surface of the outer frame are non-coplanar, and a chamber space is formed between a surface of the suspension plate and the resonance plate; and
 a piezoelectric element having a side, wherein a length of the side of the piezoelectric element is less than or equal to a side of the suspension plate, and the piezoelectric element is attached on a surface of the suspension plate, wherein when a voltage is applied to the piezoelectric element, the suspension plate is driven to undergo the bending vibration.

13. The gas detection and purification device according to claim 1, wherein the gas detection main part comprises:
 the base comprising:
 a gas-guiding-component loading region recessed from the second surface and in fluid communication with the gas-inlet groove, wherein a ventilation hole penetrates a bottom surface of the gas-guiding-component loading region, and the gas-guiding-component loading region has four positioning protrusions disposed at four corners thereof; and
 a gas-outlet groove recessed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in fluid communication with the ventilation hole, and a gas-outlet is disposed in the gas-outlet groove and in fluid communication with the environment outside the base;
 a main part piezoelectric actuator accommodated in the gas-guiding-component loading region;
 a driving circuit board covering and attached to the second surface of the base;
 a laser component positioned and disposed on and electrically connected to the driving circuit board, and accommodated in the laser loading region, wherein a light beam path emitted from the laser component passes through the transparent window and extends in a direction perpendicular to the gas-inlet groove;
 a particulate sensor positioned and disposed on and electrically connected to the driving circuit board, and disposed at a position where the gas-inlet groove intersects with the light beam path of the laser component, so that suspended particles passing through the gas-inlet groove and irradiated by a projecting light beam emitted from the laser component are detected; and
 an outer cover covering the first surface of the base and comprising a side plate, wherein the side plate has an inlet opening spatially corresponding to the gas-inlet and an outlet opening spatially corresponding to the gas-outlet, respectively,
 wherein the first surface of the base is covered with the outer cover, and the second surface of the base is covered with the driving circuit board, so that a gas-inlet path is defined by the gas-inlet groove, and a gas-outlet path is defined by the gas-outlet groove, wherein gas is drawn from the environment outside the base by the piezoelectric actuator, transported into the gas-inlet path defined by the gas-inlet groove through the inlet opening, and passes through the particulate sensor to detect the concentration of the suspended particles contained in the gas, and the gas transported through the main part piezoelectric actuator is transported out of the gas-outlet path defined by the gas-outlet groove through the ventilation hole and then discharged through the outlet opening;

wherein the base comprises a light trapping region hollowed out from the first surface to the second surface and spatially corresponding to the laser loading region, wherein the light trapping region comprises a light trapping structure having an oblique cone surface and spatially corresponding to the light beam path, wherein a light trapping distance is maintained between the transparent window and a position where the light trapping structure receives the projecting light beam.

14. The gas detection and purification device according to claim 13, wherein the main part piezoelectric actuator comprises:
- a gas-injection plate comprising a main part suspension plate and a hollow aperture, wherein the main part suspension plate is permitted to undergo a bending deformation, and the hollow aperture is formed at a center of the main part suspension plate;
- a chamber frame stacked on the main part suspension plate;
- an actuator element stacked on the chamber frame for being driven in response to an applied voltage to undergo the bending deformation in a reciprocating manner;
- an insulation frame stacked on the actuator element; and
- a conductive frame stacked on the insulation frame,
- wherein the gas-injection plate is supported and positioned on the four positioning protrusions of the gas-guiding-component loading region, and the gas-injection plate and an inner edge of the gas-guiding-component loading region define a clearance for gas to flow therethrough, a flowing chamber is formed between the gas-injection plate and the bottom surface of the gas-guiding-component loading region, a resonance chamber is formed between the actuator element, the chamber frame and the main part suspension plate, wherein an activation of the actuator element drives the gas-injection plate to move in a resonance state such that the main part suspension plate of the gas-injection plate is driven to generate the bending deformation in a reciprocating manner, and the gas is drawn in through the clearance, flows into and is discharged out of the flowing chamber, so as to achieve gas transportation.

15. The gas detection and purification device according to claim 1, wherein the main body has a length ranged from 75 mm to 110 mm, a width ranged from 50 mm to 70 mm and a height ranged from 18 mm to 32 mm.

16. The gas detection and purification device according to claim 1, wherein the main body has a length ranged from 55 mm to 95 mm, a width ranged from 55 mm to 65 mm and a height ranged from 21 mm to 29 mm.

17. The gas detection and purification device according to claim 1, wherein the main body has a length of 90 mm, a width of 60 mm and a height of 25 mm.

18. The gas detection and purification device according to claim 1, wherein the main body has a weight less than or equal to 300 g.

19. The gas detection and purification device according to claim 1, wherein the main body has a weight ranged from 150 g to 300 g.

20. The gas detection and purification device according to claim 1, wherein the main body has a weight ranged from 100 g to 200 g.

21. The gas detection and purification device according to claim 1, wherein the region from which the user draws breath has a volume of 50 cm×50 cm×50 cm.

22. The gas detection and purification device according to claim 1, wherein the communicator externally transmits the gas detection datum to an external device, and the external device obtains information in regard to the gas detection and generates an alarm indication, wherein the external device is a mobile device or a cloud processing device.

* * * * *